United States Patent
Saadat

(10) Patent No.: US 7,160,312 B2
(45) Date of Patent: Jan. 9, 2007

(54) IMPLANTABLE ARTIFICIAL PARTITION AND METHODS OF USE

(75) Inventor: Vahid Saadat, Saratoga, CA (US)

(73) Assignee: USGI Medical, Inc., San Clemente, CA (US)

( * ) Notice: Subject to any disclaimer, the term of this patent is extended or adjusted under 35 U.S.C. 154(b) by 43 days.

(21) Appl. No.: 10/288,619

(22) Filed: Nov. 4, 2002

(65) Prior Publication Data

US 2003/0093117 A1    May 15, 2003

Related U.S. Application Data

(63) Continuation-in-part of application No. 10/188,509, filed on Jul. 3, 2002, which is a continuation-in-part of application No. 09/898,726, filed on Jul. 3, 2001, now Pat. No. 6,626,899, which is a continuation-in-part of application No. 09/746,579, filed on Dec. 20, 2000, now Pat. No. 6,991,643, which is a continuation-in-part of application No. 09/602,436, filed on Jun. 23, 2000, now Pat. No. 6,669,687.

(60) Provisional application No. 60/141,077, filed on Jun. 25, 1999.

(51) Int. Cl.
*A61B 17/08* (2006.01)

(52) U.S. Cl. ................. 606/153; 606/221

(58) Field of Classification Search ........... 606/153, 606/221, 232, 148, 213, 215–217, 74, 103; 623/1.1, 1.13, 1.15, 2.37, 2.39, 2.41; 24/712, 24/713, 3.13, 17 A, 28, 21, 30.5, 714.2, 713.6
See application file for complete search history.

(56) References Cited

U.S. PATENT DOCUMENTS

| | | | |
|---|---|---|---|
| 3,166,072 A | 1/1965 | Sullivan | |
| 3,494,006 A | 2/1970 | Brumlik | |
| 4,259,959 A | 4/1981 | Walker | |
| 4,414,720 A | 11/1983 | Crooms | |
| 5,342,376 A | 8/1994 | Ruff | |
| 5,383,897 A | 1/1995 | Wholey | |
| 5,423,885 A | 6/1995 | Williams | |
| 5,582,577 A * | 12/1996 | Lund et al. | 600/204 |
| 5,584,859 A | 12/1996 | Brotz | |

(Continued)

FOREIGN PATENT DOCUMENTS

WO    WO 2000/069365 A2    11/2000

(Continued)

OTHER PUBLICATIONS

Chuttani, Ram, et al. A novel endoscopic full-thickness plicator for treatment of DERD: an animal model study. *Gastrointestinal Endoscopy*. 2002;56:116-122.

(Continued)

*Primary Examiner*—Julian W. Woo
(74) *Attorney, Agent, or Firm*—Levine Bagade Han LLP

(57) ABSTRACT

Apparatus and methods are provided for partitioning a gastro-intestinal lumen by intraluminally reducing a local cross-sectional area thereof. The apparatus comprises a plurality of anchors adapted for intraluminal penetration into a wall of the gastro-intestinal lumen to prevent migration or dislodgement of the apparatus, and a partition, which may include a drawstring or a toroidal balloon, coupled to the plurality of anchors to provide a local reduction in the cross-sectional area of the gastro-intestinal lumen.

12 Claims, 16 Drawing Sheets

U.S. PATENT DOCUMENTS

| | | | |
|---|---|---|---|
| 5,683,417 A | 11/1997 | Cooper | |
| 5,916,224 A | 6/1999 | Esplin | |
| 5,964,782 A * | 10/1999 | Lafontaine et al. | 606/213 |
| 6,419,696 B1 * | 7/2002 | Ortiz et al. | 623/2.37 |
| 6,428,550 B1 | 8/2002 | Vargas et al. | |
| 6,821,285 B1 | 11/2004 | Laufer et al. | |
| 6,835,199 B1 | 12/2004 | McGuckin, Jr. et al. | |
| 2001/0044637 A1 | 11/2001 | Jacobs et al. | |
| 2001/0051815 A1 | 12/2001 | Esplin | |
| 2002/0022861 A1 | 2/2002 | Jacobs et al. | |
| 2003/0176890 A1 | 9/2003 | Buckman et al. | |
| 2004/0122474 A1 | 6/2004 | Gellman et al. | |
| 2004/0193117 A1 | 9/2004 | Laufer et al. | |
| 2004/0193184 A1 | 9/2004 | Laufer et al. | |
| 2004/0193193 A1 | 9/2004 | Laufer et al. | |
| 2004/0193194 A1 | 9/2004 | Laufer et al. | |
| 2004/0194790 A1 | 10/2004 | Laufer et al. | |
| 2004/0210243 A1 | 10/2004 | Gannoe et al. | |
| 2004/0215216 A1 | 10/2004 | Gannoe et al. | |
| 2004/0243152 A1 | 12/2004 | Taylor et al. | |
| 2004/0249362 A1 | 12/2004 | Levine et al. | |
| 2004/0249392 A1 | 12/2004 | Mikkaichi et al. | |
| 2004/0249395 A1 | 12/2004 | Mikkaichi et al. | |
| 2005/0033320 A1 | 2/2005 | McGuckin, Jr. et al. | |
| 2005/0033328 A1 | 2/2005 | Laufer et al. | |

FOREIGN PATENT DOCUMENTS

| | | |
|---|---|---|
| WO | WO 2001/089392 A2 | 11/2001 |
| WO | WO 2001/089392 A3 | 11/2001 |
| WO | WO 2002/032345 A2 | 4/2002 |
| WO | WO 2002/060328 A1 | 8/2002 |
| WO | WO 2003/090633 A2 | 11/2003 |
| WO | WO 2003/092509 A1 | 11/2003 |
| WO | WO 2003/094785 A1 | 11/2003 |
| WO | WO 2003/105732 A1 | 12/2003 |
| WO | WO 2004/004542 A2 | 1/2004 |
| WO | WO 2004/019788 A2 | 3/2004 |
| WO | WO 2004/021894 A1 | 3/2004 |
| WO | WO 2004/056273 A1 | 7/2004 |
| WO | WO 2004/084808 A2 | 10/2004 |
| WO | WO 2004/103189 A1 | 12/2004 |
| WO | WO 2005/004727 A1 | 1/2005 |

OTHER PUBLICATIONS

Mason, Edward E. Development and Future of Gastroplasties for Morbid Obesity. *Arch Surg*. 2003;138:361-366.

US 6,447,535, 09/2002, Jacobs et al. (withdrawn)

* cited by examiner

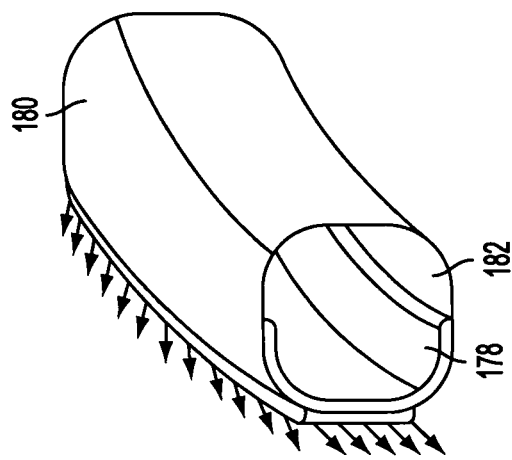
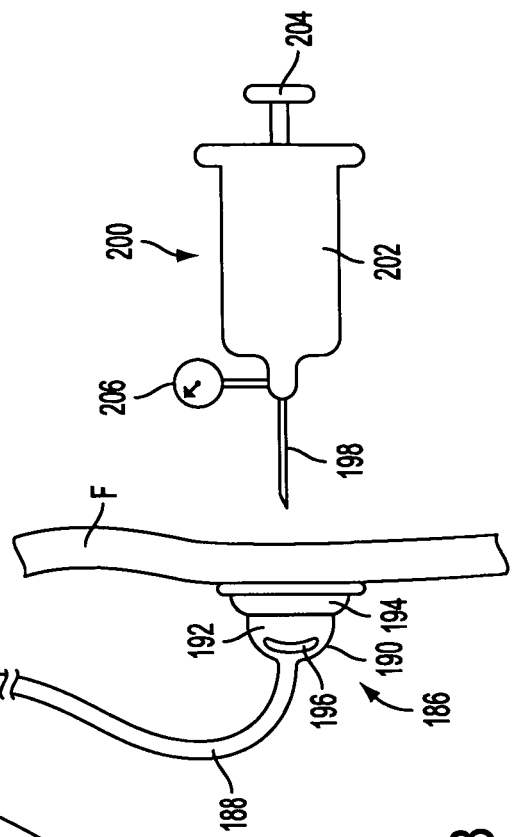
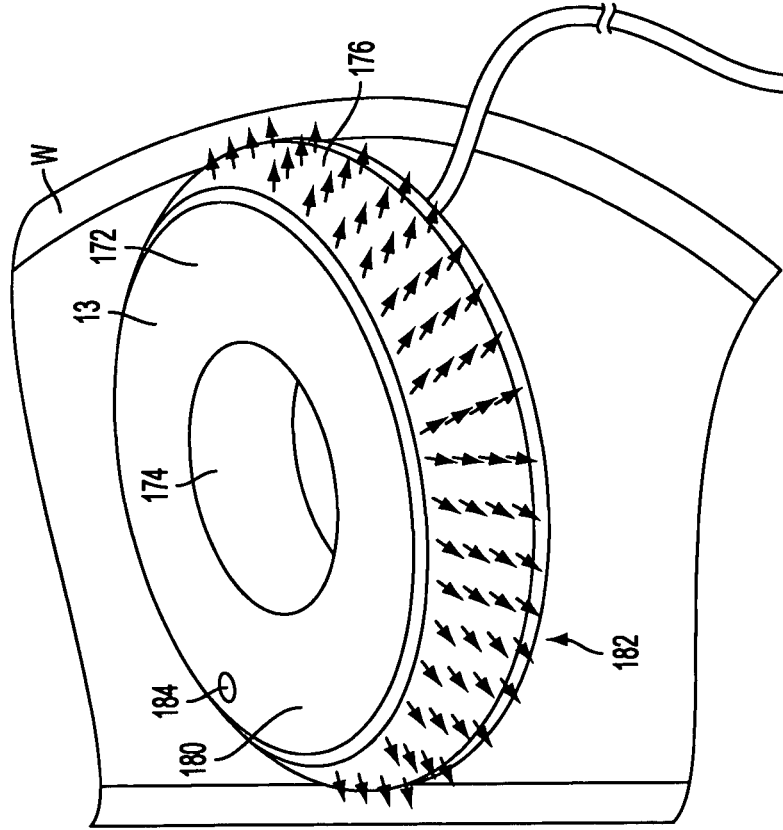
FIG. 19
FIG. 18

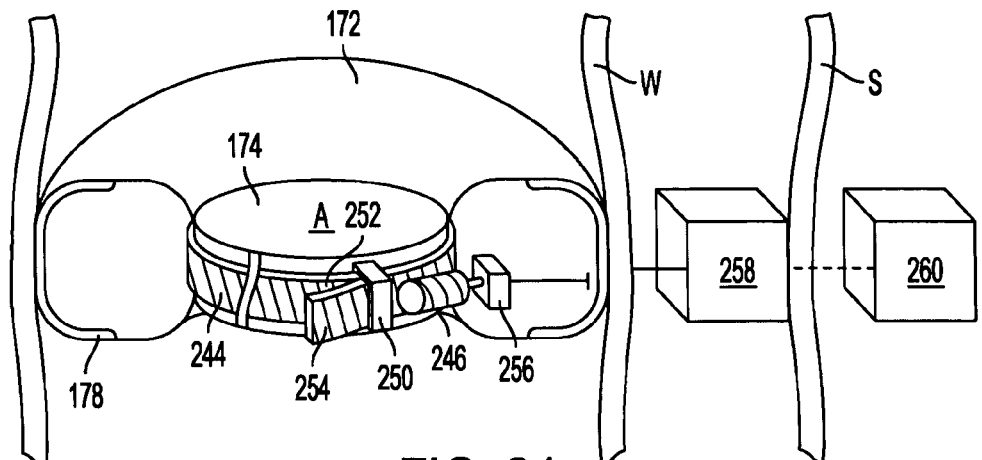
FIG. 24
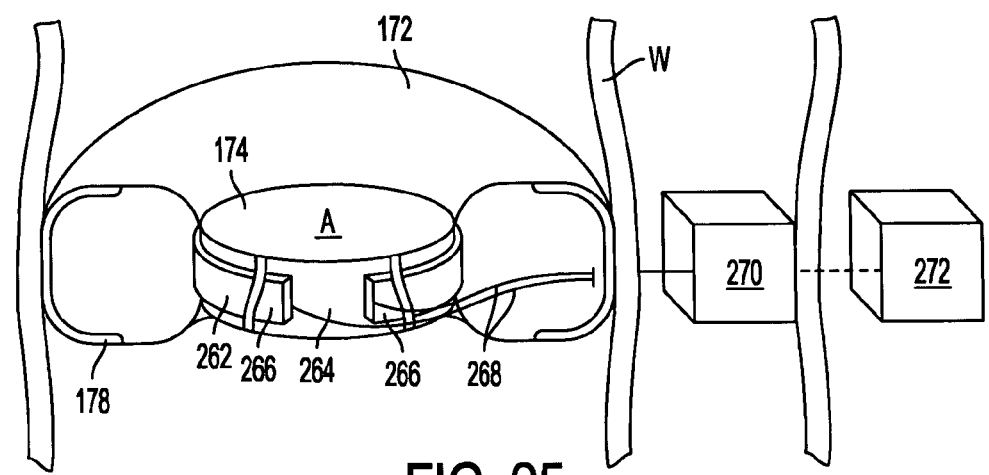
FIG. 25
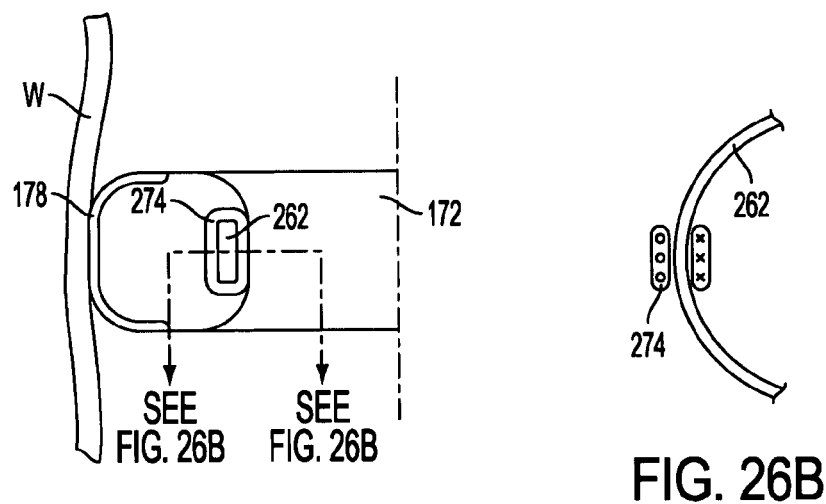
FIG. 26A
FIG. 26B

IMPLANTABLE ARTIFICIAL PARTITION AND METHODS OF USE

REFERENCE TO RELATED APPLICATIONS

This application is a continuation-in-part of U.S. patent application Ser. No. 09/746,579, filed Dec. 20, 2000, now U.S. Pat. No. 6,991,643 and a continuation-in-part of copending commonly assigned U.S. patent application Ser. No. 10/188,509, filed Jul. 3, 2002, which is a continuation-in-part of U.S. patent application Ser. No. 09/898,726, filed Jul. 3, 2001, now U.S. Pat. No. 6,626,899 which is a continuation-in-part of U.S. patent application Ser. No. 09/602,436, filed Jun. 23, 2000, now U.S. Pat. No. 6,669,687 which claims benefit from U.S. provisional patent application Ser. No. 60/141,077, filed Jun. 25, 1999, the entireties of which are incorporated herein by reference.

FIELD OF THE INVENTION

The present invention relates to apparatus and methods for partitioning a gastro-intestinal ("GI") lumen to provide a localized reduction in a cross-sectional area of the GI lumen.

BACKGROUND OF THE INVENTION

Extreme or morbid obesity is a serious medical condition pervasive in the United States and other countries. Its complications include hypertension, diabetes, coronary artery disease, stroke, congestive heart failure, multiple orthopedic problems and pulmonary insufficiency with markedly decreased life expectancy.

Several surgical techniques have been developed to treat morbid obesity, e.g., bypassing an absorptive surface of the small intestine, or reducing the stomach size. These procedures are difficult to perform in morbidly obese patients and present numerous life-threatening post-operative complications.

U.S. Pat. Nos. 4,416,267 and 4,485,805 to Garren et al. and Foster, Jr., respectively, propose disposal of an inflated bag within a patient's stomach to decrease the effective volume of the stomach that is available to store food. Accordingly, the patient is satiated without having to consume a large amount of food. A common problem with these inflated bags is that, since the bags float freely within the patient's stomach, the bags may migrate to and block a patient's pyloric opening, the portal leading from the stomach to the duodenum, thereby restricting passage of food to the remainder of the gastro-intestinal tract.

Apparatus and methods also are known in which an adjustable elongated gastric band is disposed around the outside of a patient's stomach near the esophagus to form a collar that, when tightened, squeezes the stomach into an hourglass shape that limits the amount of food that a patient comfortably may consume. An example of an adjustable gastric band is the LAP-BAND® made by INAMED Health of Santa Barbara, Calif.

Numerous disadvantages are associated with using the adjustable gastric band. First, the band may be dislodged if the patient grossly overeats, thereby requiring additional invasive surgery to either reposition or remove the band. Similarly, overeating may cause the band to injure the stomach wall if the stomach over-expands. The laparoscopic disposal of the gastric band around the stomach requires a complex procedure, requires considerable skill on the part of the clinician, and is not free of dangerous complications. To dispose the gastric band around a patient's stomach, a clinician must perform a surgical procedure to gain access to the patient's stomach from outside the stomach. This is typically performed using the narrow field of vision provided by a conventional laparoscope, and presents a risk that the clinician inadvertently may perforate the stomach, damage major organs and vessels disposed in the vicinity of the stomach, such as the liver, kidneys, and the abdominal aorta, damage the vagus nerve and/or cause numerous other complications associated with surgery.

In view of the foregoing, it would be desirable to provide apparatus and methods for partitioning a GI lumen by intraluminally reducing a local cross-sectional area thereof.

It also would be desirable to provide apparatus and methods for partitioning a GI lumen without substantially altering a native shape of the lumen.

It further would be desirable to provide apparatus for partitioning a GI lumen that decreases the risk that the apparatus may become dislodged.

It still further would be desirable to provide apparatus for partitioning a GI lumen that is easy to deliver.

It even further would be desirable to provide apparatus and methods for partitioning a GI lumen that reduces the risk of damage to surrounding organs, vessels, and nerves.

It also would be desirable to provide apparatus and methods for partitioning a GI lumen, in which a cross-sectional area of a partition defined by the apparatus may be endoscopically adjusted.

It additionally would be desirable to provide apparatus and methods for partitioning a GI lumen, in which a cross-sectional area of a partition defined by the apparatus may be dynamically adjusted responsive to the pressure of food proximal to the apparatus.

It also would be desirable to provide apparatus and methods for partitioning a GI lumen, in which a cross-sectional area of a partition defined by the apparatus may be remotely adjusted via wireless communication with an external control unit.

SUMMARY OF THE INVENTION

In view of the foregoing, it is an object of the present invention to provide apparatus and methods for partitioning a GI lumen by intraluminally reducing a local cross-sectional area thereof.

It also is an object of the present invention to provide apparatus and methods for partitioning a GI lumen without substantially altering a native shape of the lumen.

It further is an object of the present invention to provide apparatus for partitioning a GI lumen that decreases the risk that the apparatus may become dislodged.

It still further is an object of the present invention to provide apparatus for partitioning a GI lumen that is easy to deliver.

It even further is an object of the present invention to provide apparatus and methods for partitioning a GI lumen that reduces the risk of damage to surrounding organs, vessels, and nerves.

It also is an object of the present invention to provide apparatus and methods for partitioning a GI lumen, in which a cross-sectional area of a partition defined by the apparatus may be endoscopically adjusted.

It additionally is an object of the present invention to provide apparatus and methods for partitioning a GI lumen, in which a cross-sectional area of a partition defined by the apparatus may be dynamically adjusted responsive to the pressure of food proximal to the apparatus.

It is another object of the present invention to provide apparatus and methods for partitioning a GI lumen, in which a cross-sectional area of a partition defined by the apparatus may be remotely adjusted via wireless communication with an external control unit.

These and other objects of the present invention are accomplished by providing apparatus and methods for partitioning a GI lumen by intraluminally reducing a local cross-sectional area thereof. The localized reduction redefines the lumen into upper and lower portions. The reduced volume of the upper portion, as compared to the native volume of the GI lumen, constrains the amount of food that a patient consumes by providing a feeling of satiety after only a small amount of food has been consumed. Furthermore, the reduced cross-sectional area of the GI lumen reduces the rate in which food passes through the GI lumen. This increases the residence time of the food within the upper portion of the GI lumen, thereby enhancing the feeling of satiety.

In a preferred embodiment, the apparatus of the present invention includes a plurality of anchors configured to intraluminally penetrate into a wall of the GI lumen to prevent dislodgement or migration of the apparatus. The apparatus of the present invention further includes a partition coupled to the plurality of anchors to provide a localized reduction in a cross-sectional area of the GI lumen.

The plurality of anchors may include a substrate having a multiplicity of barbs, a plurality of struts optionally covered by a membrane, a barbed distal end, an elongated shaft that assumes a coil-shape when expanded, an enclosure containing water-swellable gel, and combinations thereof. Also provided are delivery catheters for delivering the plurality of anchors without injuring surrounding organs and vessels.

The partition may include a biocompatible drawstring that, when threaded through fixture points disposed on the plurality of anchors, defines a stoma having an adjustable cross-sectional area. Adjustment of the stoma may be performed endoscopically or through actuation of an implanted motor coupled to the drawstring.

Alternatively, the partition may include a toroidal balloon that also defines a stoma having an adjustable cross-sectional area. In a preferred embodiment, the toroidal balloon incorporates a membrane that partially lines the balloon, and constrains proximal distal and outward radial expansion of the balloon. Accordingly, when the balloon is inflated, the balloon expands in an inwardly radial direction into the stoma, thereby decreasing the cross-sectional area thereof.

To adjust the cross-sectional area of the balloon stoma, the balloon may be endoscopically inflated through a re-sealable port integral with the balloon. The balloon may also be coupled in fluid communication with a subcutaneously implanted inflation port through which an inflation medium, such as air or water, may be introduced with a syringe, or with a reservoir operably coupled to a pump. Alternatively, the balloon may comprise a substantially annular band having an adjustable diameter to adjust the cross-sectional area of the stoma around which it is disposed. The annular band may serve as a worm gear keyed to a worm that is coupled to a motor, or be made from a thermally-responsive shape memory alloy having two configurations of differing diameters.

According to another aspect of the present invention, the stoma diameter may dynamically adjust responsive to the pressure of food in the GI lumen proximal to an upper surface of the toroidal balloon.

To measure the diameter of the stoma defined by the toroidal balloon after the balloon is implanted, a relationship between the stoma diameter and the pressure of the balloon may be provided or determined. Alternatively, a plurality of ultrasound transducers or a conductive band having a length-dependent resistance may be disposed around the balloon stoma.

To prevent food from shunting between the partition and the lumen wall, the apparatus of the present invention may provide a cuff configured for attachment to the lumen wall proximal to the plurality of anchors and the partition, and to direct food in the GI lumen to pass through the stoma defined by the drawstring or the toroidal balloon. Alternatively, the toroidal balloon may be adapted to enhance sealing engagement of the balloon to the lumen wall. More specifically, the plurality of anchors may be coupled to the balloon so that, when the balloon expands into the stoma during inflation, the anchors pull the lumen wall into a plurality of concavities disposed around the balloon.

Methods of using the apparatus of the present invention also are provided.

BRIEF DESCRIPTION OF THE DRAWINGS

Further features of the present invention, its nature and various advantages will be more apparent from the accompanying drawings and the following detailed description of the preferred embodiments, in which:

FIG. 18 is a schematic perspective view of an alternative embodiment of the partition of the present invention;

FIG. 19 is a schematic cross-sectional view of the partition of FIG. 18;

FIG. 24 is a schematic cross-sectional perspective view of an alternative embodiment of the partition of FIG. 18, in which a cross-sectional area of a stoma defined by the partition is adjusted through actuation of a worm gear assembly;

FIG. 25 is a schematic cross-sectional perspective view of another alternative embodiment of the partition of FIG. 18, in which a cross-sectional area of a stoma defined by the partition is adjusted by ohmically heating a thermally-responsive shape memory alloy;

FIG. 26A is a schematic cross-sectional view of yet another alternative embodiment of the partition of FIG. 18, in which a cross-sectional area of a stoma defined by the partition may be adjusted by inductively heating a thermally-responsive shape memory alloy;

FIG. 26B is a schematic cross-sectional view of a toroidal inductor of FIG. 26A disposed surrounding the thermally-responsive shape memory alloy;

DETAILED DESCRIPTION OF THE INVENTION

The present invention relates to apparatus and methods for partitioning a GI lumen. A localized reduction in a cross-sectional area of the GI lumen is created intraluminally, thereby defining upper and lower portions of the lumen. The reduced volume of the upper portion, as compared to the native volume of the GI lumen, constrains the amount of food a patient consumes by providing a feeling of satiety after only a small amount of food is consumed. Furthermore, the reduced cross-sectional area of the GI lumen reduces the rate in which food passes through the GI lumen. This increases the residence time of the food within the upper portion of the GI lumen, thereby enhancing the feeling of satiety. It will be obvious to one of skill in the art that, while the following written description illustratively describes use of the apparatus and methods of the present invention to partition a patient's stomach, the present invention may be implanted anywhere in the gastro-intestinal tract, e.g., esophagus, and within a variety of body lumens requiring restriction of flow of materials therethrough.

Figure 1:
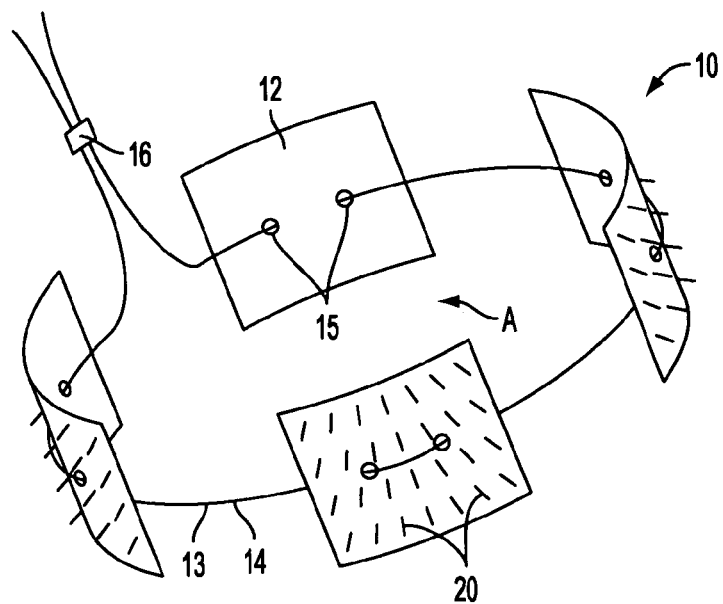
FIG. 1 is a schematic perspective view of a plurality of anchors coupled to a partition of the present invention.
Figure 2:
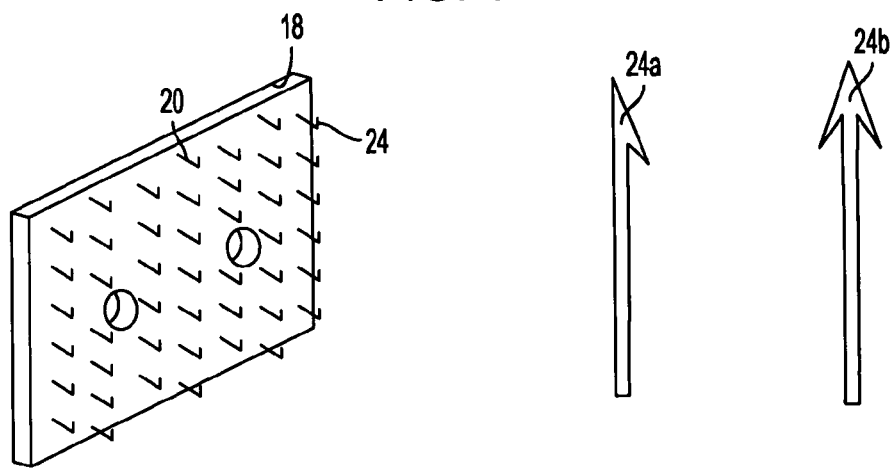
FIG. 2 is a schematic perspective view of one of the plurality of anchors of FIG. 1.

Referring to FIGS. 1–2, a first embodiment of apparatus 10 of the present invention schematically is illustrated in its deployed configuration. Apparatus 10 includes plurality of anchors 12 configured to penetrate into a wall of the GI lumen to prevent dislodgement or migration of the apparatus. Apparatus 10 also includes partition 13, e.g., drawstring 14, coupled to plurality of anchors 12 through fixture points 15, and fastener 16 that maintains tension applied to drawstring 14. When anchors 12 are engaged to the lumen wall and drawstring 14 is coupled to the anchors, drawstring 14 defines a stoma having cross-sectional area A that is substantially coincident with a local cross-sectional area of the GI lumen. Accordingly, when tension is applied to drawstring 14, each anchor 12 is drawn closer to adjacent anchors. Since anchors 12 are engaged to the lumen wall, this action cinches the GI lumen to form a partition that defines a localized reduction in the cross-sectional area of the GI lumen.

Figure 4:
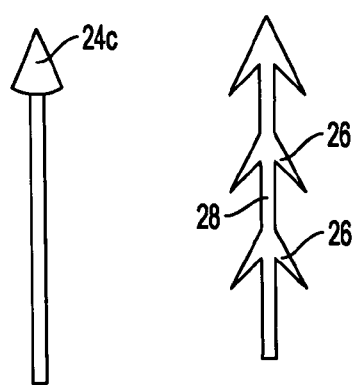
FIG. 4 are schematic views of alternative embodiments of the plurality of anchors of the present invention.

Each anchor 12 incorporates substrate 18 having multiplicity of barbs 20 and at least one fixture point 15, e.g., an eyelet, through which drawstring 14 may be threaded. Preferably, substrate 18 is made of a flexible material to permit the anchor to conform to the surface of the lumen wall. Each barb 20 has sharpened distal end 24 that enables the barb to penetrate into the lumen wall, and to resist disengagement therefrom when tensile forces applied to drawstring 14 are transmitted to anchor 12. Distal ends 24 of barbs 20 may have a harpoon configuration (24a in FIG. 4), an arrow configuration (24b in FIG. 4), or a conical configuration (24c in FIG. 4). Alternatively, barbs 20 may include additional ribs, hooks, or projections 26 disposed along shanks 28 of barbs 20 to further enhance the engagement of the barbs to the lumen wall.

Figure 3:
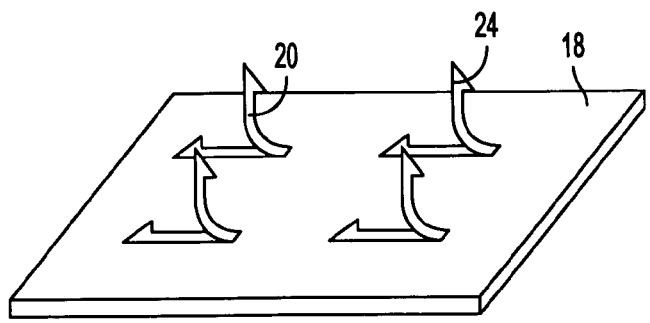
FIG. 3 is a schematic close-up view of an alternative embodiment of one of the plurality of anchors.

FIG. 3 depicts a method of manufacturing anchor 12, wherein the barbs are integrally formed from substrate 18 comprising a thin, flexible sheet of biocompatible polymer or metal alloy. Barbs 20 are die cut from substrate 18, and then bent out of the plane of substrate 18 to expose sharpened distal ends 24. In a preferred embodiment, barbs 20 are bent at either an acute or an obtuse angle with respect to substrate 18 so that, when the angled barbs are engaged to the lumen wall in a downward radial direction, a distal force applied by food entering the GI lumen will less likely disengage the anchors. Accordingly, the biocompatible polymer or metal alloy preferably comprises a material that provides barbs 20 with sufficient rigidity to penetrate the lumen wall during application, and to withstand the tensile forces and moments expected during normal use, i.e., so barbs 20 cannot be pulled out of the lumen wall, and shanks 28 will not fracture in large numbers.

Figure 5:
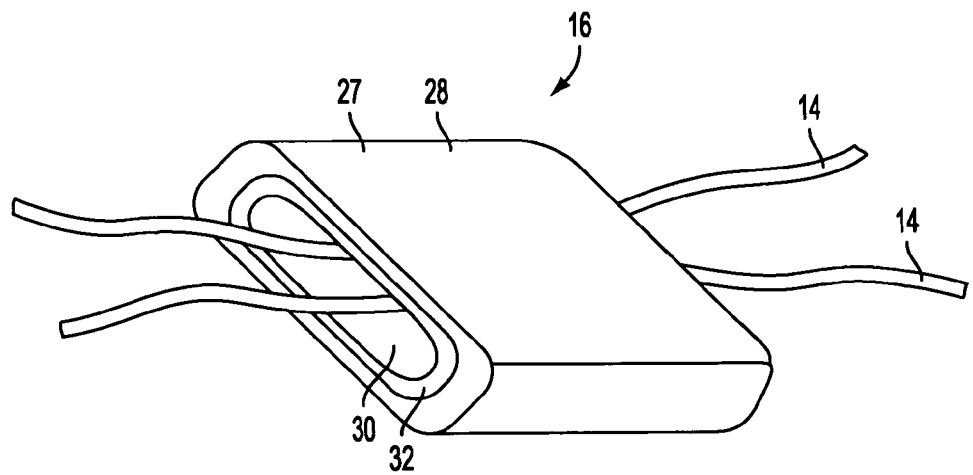
FIG. 5 is a schematic perspective view of a fastener for maintaining tension applied to the partition of FIG. 1.
Figure 6:
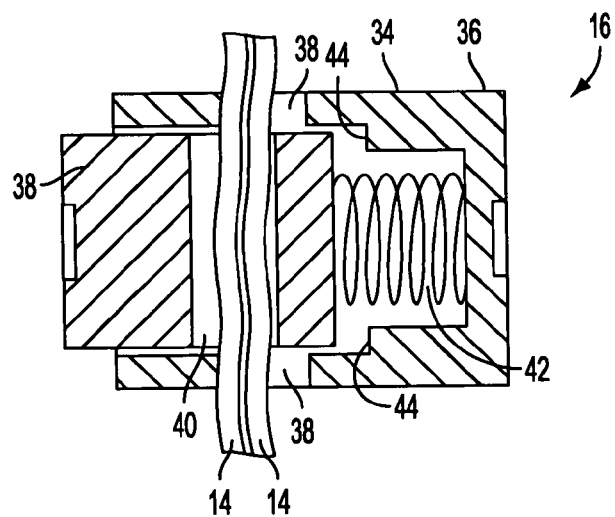
FIG. 6 is a schematic perspective view of an alternative embodiment of a fastener for maintaining tension applied to the partition of FIG. 1.

Referring now to FIG. 5, fastener 16 is described in detail. Fastener 16 includes collar 27 having body 28 and channel 30 through which drawstring 14 may freely translate prior to crimping. Once fastener 16 is crimped by a mallet/anvil assembly to be described in greater detail hereinbelow, drawstring 14 is restrained from freely translating through channel 30. This permits fastener 16 to maintain tension applied to drawstring 14, and thus the local reduction in the cross-sectional area of the GI lumen. Optionally, to decrease the likelihood that tension applied to drawstring 14 may be inadvertently lost through slippage of the drawstring through channel 30, body 28 may incorporate lining 32 to further enhance uni-directional friction between body 28 and drawstring 14 to reduce the risk of slippage. Lining 32 may comprise a biocompatible, elastomeric material, and/or a lining having barbs or a roughened surface.

Alternatively, to enable cross-sectional area A defined by drawstring 14, and thus the localized reduction in the cross-sectional area of the GI lumen, to be adjusted, fastener 16 may comprise adjustable clip 34 having housing 36 and engagement piece 38 translatably disposed within housing 36. Housing 36 includes first bore 38, which is disposed orthogonal to the direction of translation of engagement piece 38, and has a cross-sectional area that accommodates unrestricted movement of drawstring 14 therethrough. Likewise, engagement piece 38 also incorporates second bore 40 disposed parallel to first bore 38, and having a cross-sectional area that will accommodate unrestricted movement of drawstring 14 therethrough. Also included within clip 34 is spring 42 that is disposed between housing 36 and engagement piece 38 to bias engagement piece 38 so that first and second bores 38 and 40 are misaligned absent an external force to counter the force of spring 42. When the first and second bores are misaligned, drawstring 14 is constrained from freely translating therethrough. When an external force is applied to counter the outward biasing force of spring 42, engagement piece 38 translates within housing 36 until engagement piece 38 contacts ledge 44. At this point, first and second bores 38 and 40 are aligned, and drawstring 14 may move freely therethrough to adjust the tension applied to drawstring 14. Advantageously, this permits the reduction in the cross-sectional area of the GI lumen to be adjusted, thereby providing control over the rate that food passes through the GI lumen.

Figure 7:
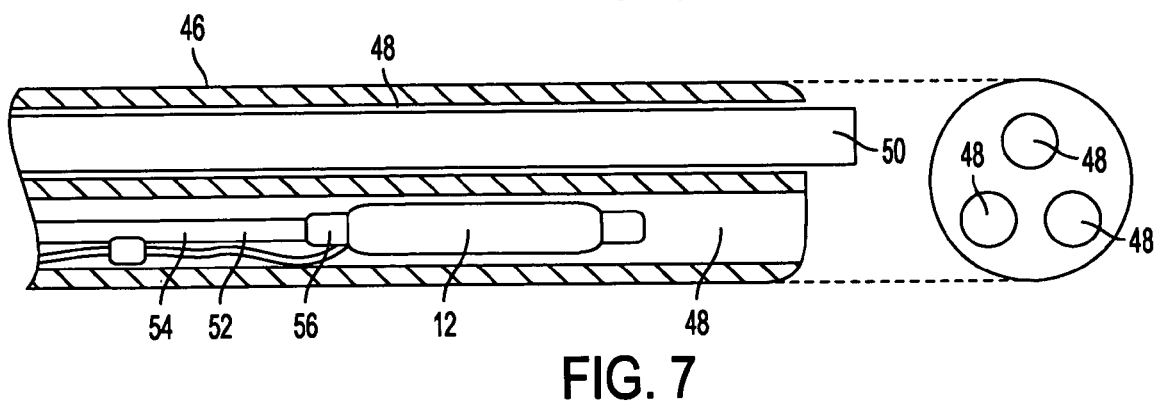
FIG. 7 are perspective side sectional and frontal views of a guide catheter that accepts an endoscope and a delivery catheter for delivering the apparatus of the present invention.
Figure 8B:
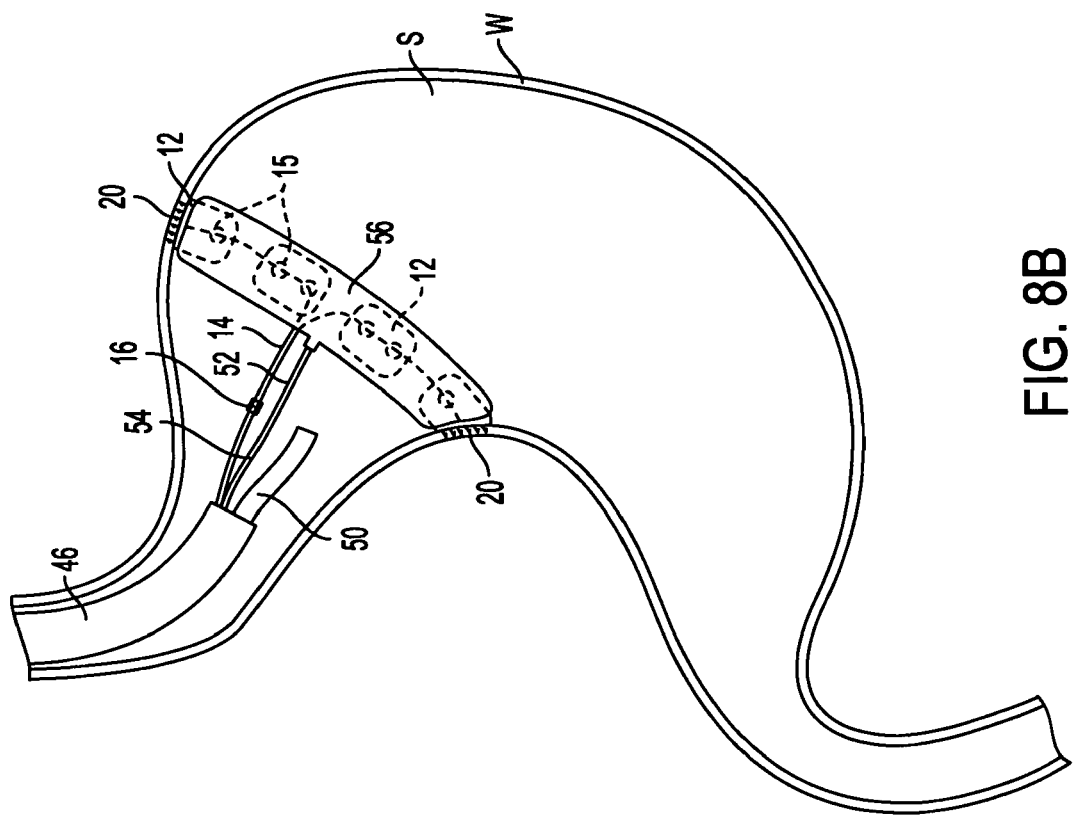
FIGS. 8A–8E are schematic side views depicting a method of using the apparatus of the present invention.
Figure 8A:
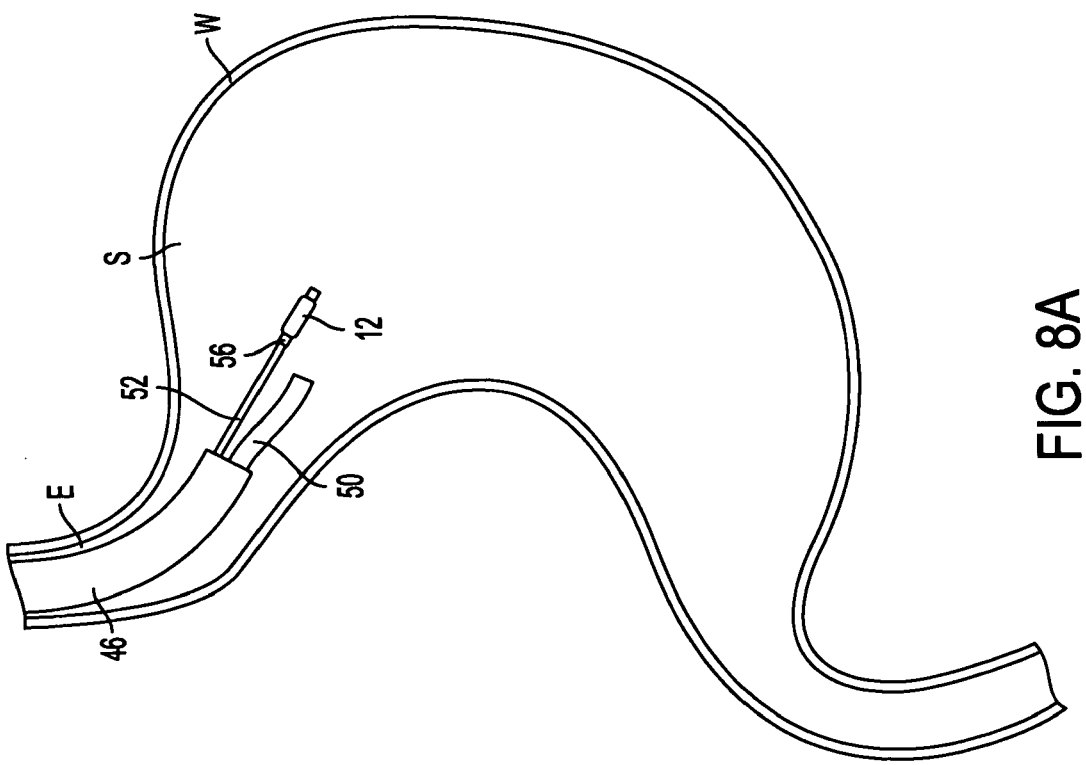
Figure 8D:
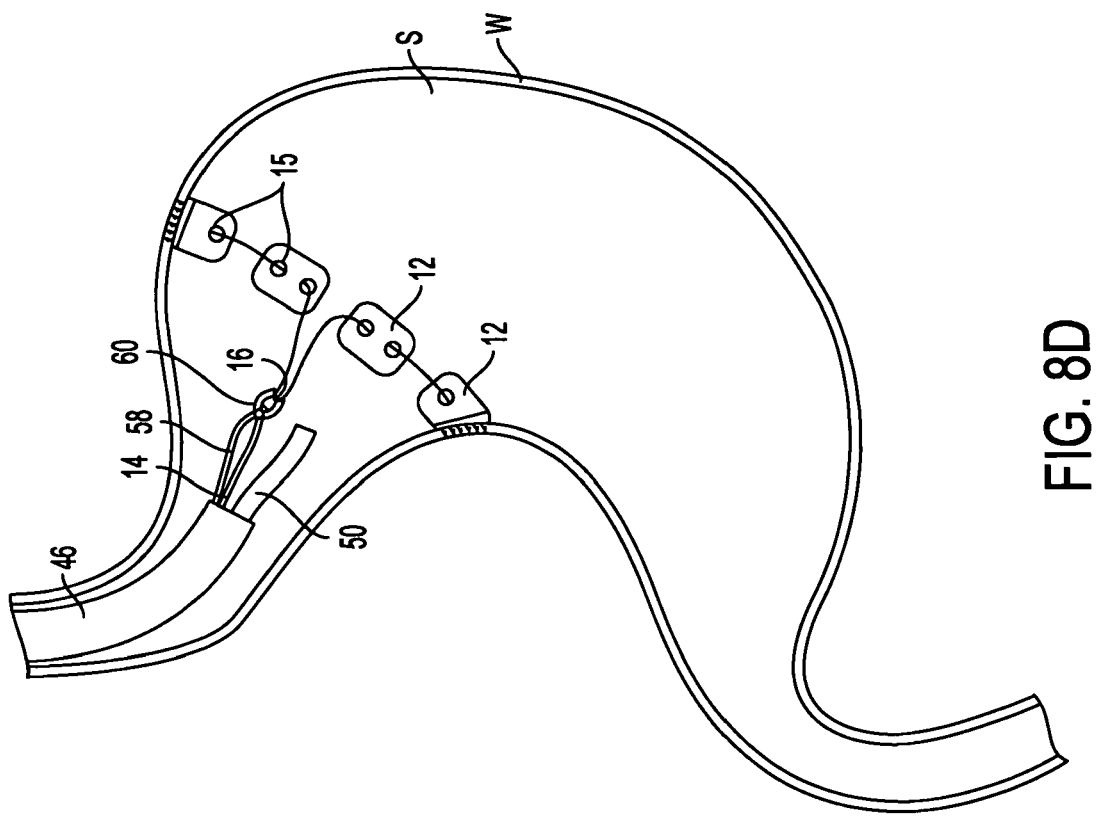
Figure 8C:
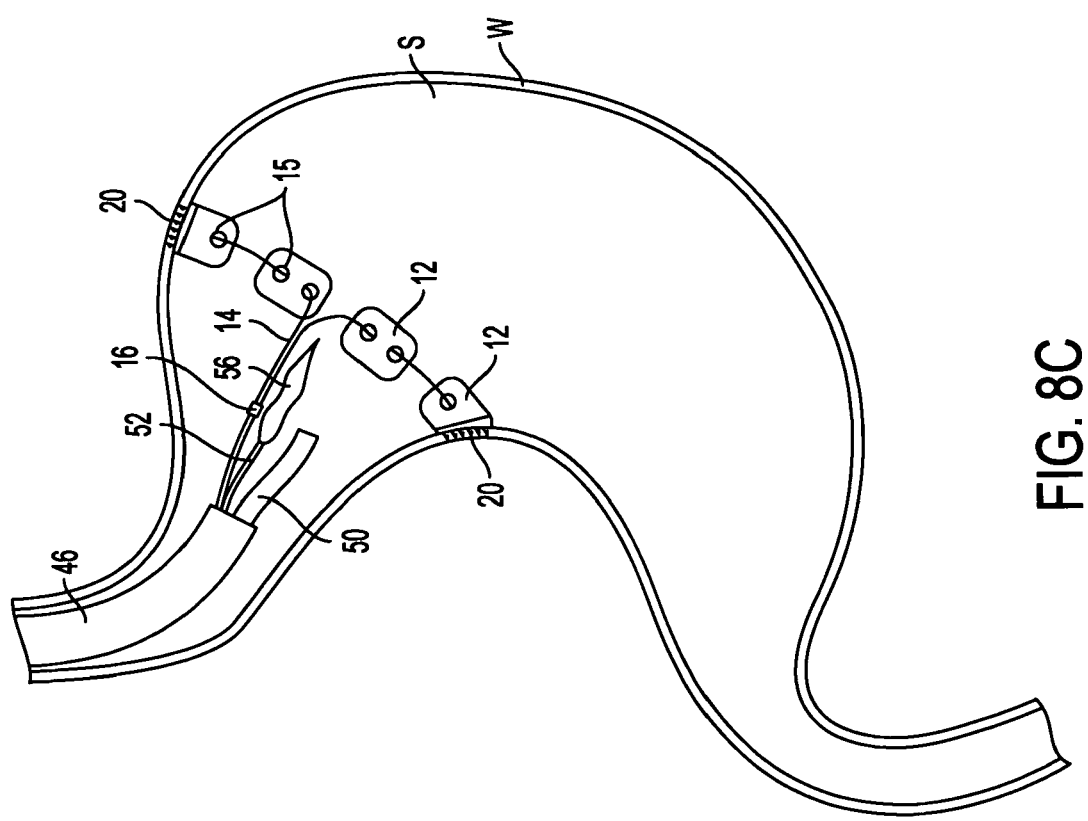

Referring now to FIG. 7, guide catheter 46 is described. To facilitate endoscopic delivery of apparatus 10 of the present invention, guide catheter 46 includes plurality of lumens 48 that accommodate advancement of endoscope 50, per se known in the art. Plurality of lumens 48 also accommodates advancement of delivery catheter 52 having lumen 54 coupled in fluid communication with inflatable member 56, which is disposed on the distal end of delivery catheter 52. As illustrated in greater detail in FIG. 8B, plurality of anchors 12 are removably attached to an external surface of inflatable member 56 by, e.g., a weak adhesive. In FIG. 7, plurality of anchors 12 are disposed on inflatable member 56 in their delivery configuration so that they may be advanced through lumen 48 of guide catheter 46.

Preferably, drawstring 14 is pre-threaded through fixture points 15 prior to adherence of anchors 12 to inflatable member 56. Drawstring 14 also preferably has sufficient length to span lumen 48 proximal to inflatable member 56 so that a clinician can grasp the ends of drawstring 14 (not shown) to facilitate delivery of apparatus 10 in a manner described in greater detail hereinbelow. Furthermore, fastener 16 preferably is engaged to drawstring 14 prior to advancement of delivery catheter 52 into lumen 48 to facilitate delivery of apparatus 10. It will be apparent to one of ordinary skill in the art that, while distal ends 24 of barbs 20 are sufficiently sharp to penetrate the lumen wall of the GI lumen, the distal ends also preferably are sufficiently dull to avoid puncture of inflatable member 56.

Referring now to FIGS. 8A–8E, a method of using apparatus 10 is provided. Guide catheter 46 is advanced through esophagus E and disposed in a proximal portion of stomach S. Endoscope 50 and delivery catheter 52 then are advanced through the guide catheter, with plurality of anchors 12 disposed surrounding inflatable member 56. Under the visual guidance provided by endoscope 50, delivery catheter 52 is positioned within stomach S. Thereafter, inflation fluid, e.g., air or water, is introduced through lumen 54 of catheter 52 into inflatable member 56 to expand the inflatable member until plurality of anchors 12 forcefully contact lumen wall W of stomach S. The pressure from the expansion of inflatable member 56 causes barbs 20 to penetrate into lumen wall W. Since distal ends 24 of barbs 20 (see FIG. 4) are configured to resist disengagement of the barbs from lumen wall W, and anchors 12 are adhered to inflatable member 56 with a weak adhesive, anchors 12 disengage from inflatable member 56 without pulling barbs 20 from lumen wall W when the inflatable member is deflated. Thereafter, delivery catheter 52 and deflated inflatable member 56 are removed from the patient through guide catheter 46.

Figure 8E:
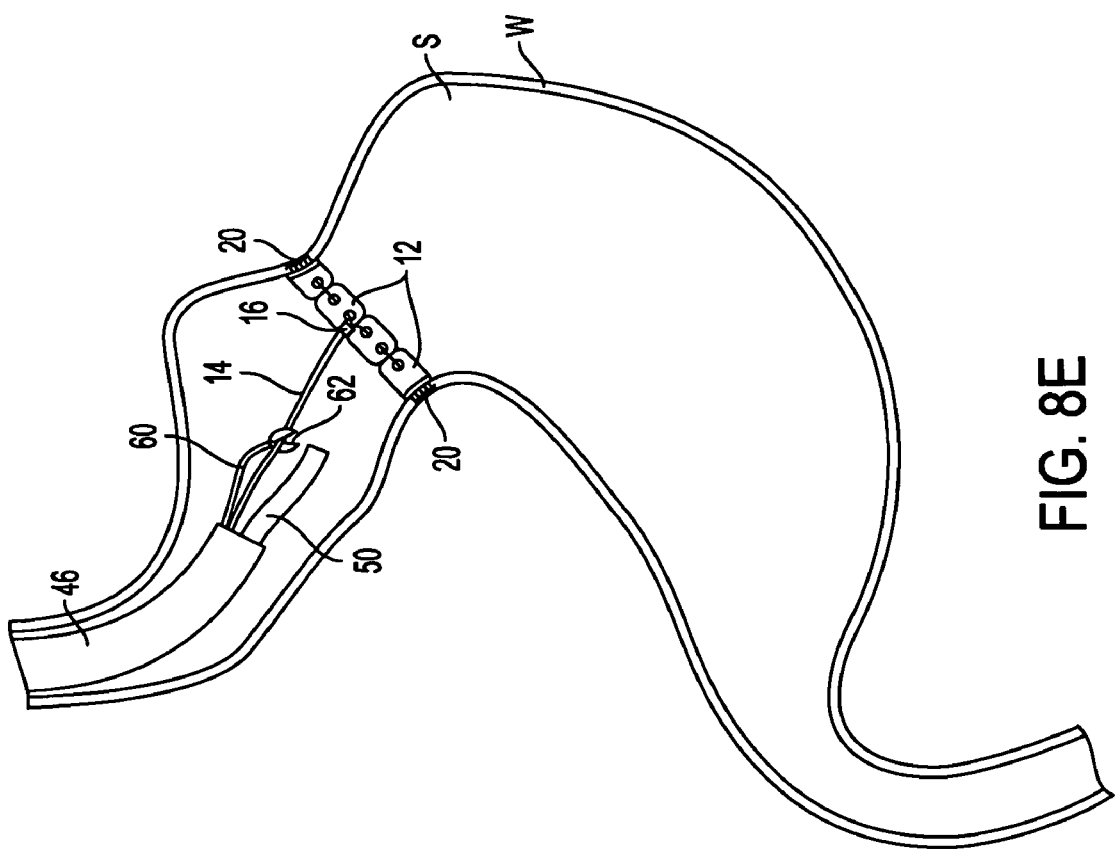

To tighten drawstring 14, and thereby cause a localized reduction in the cross-sectional area of stomach S, catheter 58, having end effector 60, is provided for disposal within stomach S through guide catheter 46. End effector 60 comprises a mallet/anvil assembly that can grasp fastener 16 by manipulating an actuator (not shown) disposed on a proximal end of catheter 58. After end effector 60 is engaged to fastener 16, concurrent application of a distal force to catheter 58 and a proximal force to the ends of drawstring 14 distally urges fastener 16 along drawstring 14. Continual advancement of fastener 16 tightens drawstring 14, drawing each anchor 12 closer to adjacent anchors. Since anchors 12 are engaged to lumen wall W, this causes a localized reduction in the cross-sectional area of stomach S, as shown in FIG. 8E.

Once sufficient tension has been applied to drawstring 14 to obtain the desired reduction in the cross-sectional area of stomach S, end effector 60 may be disengaged from fastener 16 and proximally retracted from guide catheter 46. To reduce drawstring 14 to an appropriate length within stomach S, catheter 62 having end effector 64 comprising a pair of scissors is advanced through guide catheter 46. Once drawstring 14 has been cut, guide catheter 46 is removed from the patient along with catheter 62, endoscope 50 and the severed portion of drawstring 14 that is disposed through guide catheter 46.

Of course, it will be evident that anchors 12 may be delivered to stomach S without drawstring 14 having been pre-threaded through fixture points 15 prior to adhesion of the anchors to inflatable member 56. In such a case, after anchors 12 have been engaged to lumen wall W, a catheter having an appropriate end effector may be inserted through guide catheter 46 to thread drawstring 14 through fixture points 15.

Figure 9:
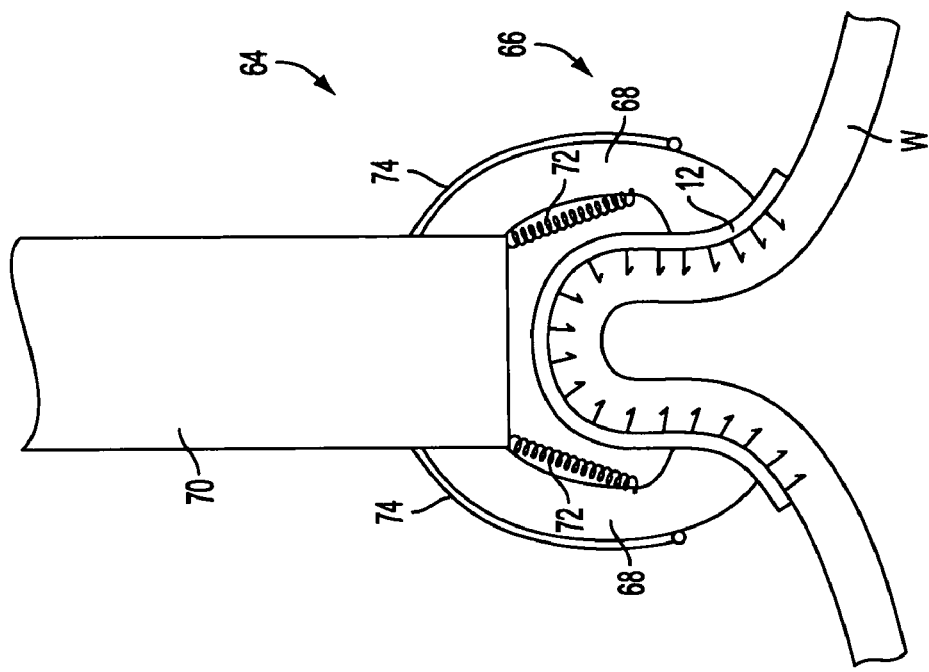
FIG. 9 is a schematic side view of an alternative delivery catheter for delivering the plurality of anchors of FIG. 1.

FIG. 9 describes an alternative delivery catheter for engagement of anchors 12 to lumen wall W. Rather than having an inflatable member, delivery catheter 64 has end effector 66, which comprises a mallet/anvil assembly. More specifically, end effector 66 includes two pinchers 68 rotatably mounted to the distal end of catheter body 70. Pinchers 68 are coupled to springs 72, which bias pinchers 68 closed in its equilibrium state. To grasp an object with end effector 66, a proximal force may be applied to wires 74, which are attached to pinchers 68. A proximal force of sufficient magnitude overcomes the spring forces applied by springs 72, opening pinchers 68 for engagement with an object therebetween. It will be apparent to one of ordinary skill in the art that minor modifications may be made to the attachment points of springs 72 and wires 74 to bias pinchers 68 open.

In operation, anchor 12 is placed against an inner surface of lumen wall W. Pinchers 68 are actuated to grasp anchor 12 and lumen wall W so that they fold into the space between pinchers 68. Pressure applied by pinchers 68 penetrates barbs 20 into lumen wall W, thereby engaging anchor 12 thereto.

Figure 10:
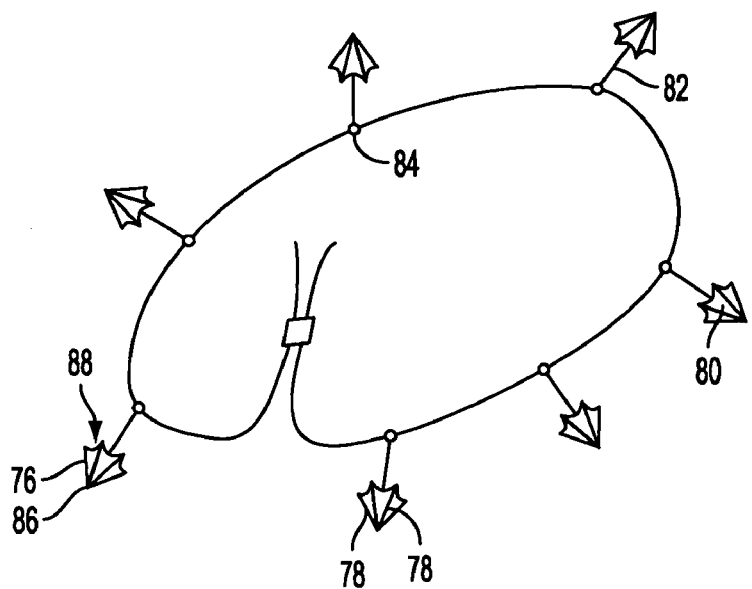
FIG. 10 is a schematic perspective view of an alternative embodiment of the plurality of anchors of the present invention coupled to the partition of FIG. 1.

Referring now to FIG. 10, an alternative embodiment of the plurality of anchors of the present invention is described. Each anchor 76 incorporates multiplicity of struts 78 that optionally are covered by membrane 80, shank 82 preferably having a length approximately equal to or slightly less than the thickness of lumen wall W, and fixture point 84, e.g., an eyelet, through which drawstring 14 may be threaded. Struts 78 are re-configurable from a reduced delivery profile, in which struts 78 closely approximate shank 82, to an expanded profile shown in FIG. 10, in which struts 78 form a conical shape. The conical shape provides a sharp tip at distal end 86 of anchor 76 to facilitate penetration of lumen wall W. Moreover, the conical shape formed by struts 78 provides wide base 88 at the proximal end of the struts to decrease the risk that anchor 76 may retract through lumen wall W when drawstring 14 is tensioned. Struts 78 may completely penetrate through lumen wall W to deploy distal to the lumen wall, as shown in FIG. 12B, or may penetrate partially through lumen wall W to deploy within the lumen wall.

Figure 11A:
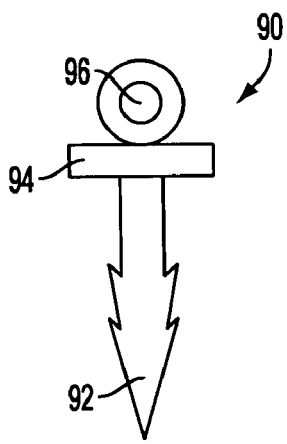
FIGS. 11A–11D are schematic side views of further alternative embodiments of the plurality of anchors of the present invention.

Alternative embodiments of anchors 76 are provided in FIGS. 11A–11D. In FIG. 11A, anchor 90 is shown having barbed distal end 92, optional stop 94, and fixture point 96, e.g., an eyelet. Optional stop 94 is disposed proximal to barbed distal end 92 to decrease the likelihood that anchor 90 may penetrate too far into lumen wall W. It will be apparent that, while FIG. 11A illustrates distal end 92 having two barbs, more or less barbs also may be provided.

Figure 11B:
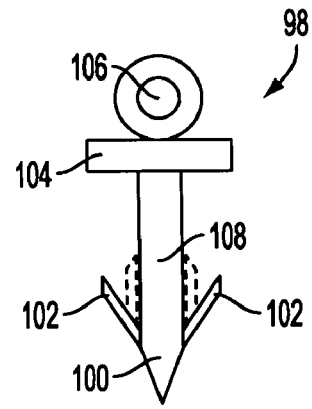

In FIG. 11B, anchor 98 has sharp distal end 100, pivoting struts 102, stop 104, and fixation point 106. When disposed in a reduced delivery profile to penetrate lumen wall W, pivoting struts 102 may be disposed flush against shank 108 of anchor 98, as shown by the dashed lines. After struts 102 are inserted past lumen wall W, pivoting struts 102 assume an expanded profile in which the struts extend outwardly so that proximal ends of the struts abut against an outer surface of the lumen wall when a proximally directed force is applied to the anchor. This decreases the risk that anchor 98 may retract through lumen wall W when drawstring 14 is tensioned.

Figure 11C:
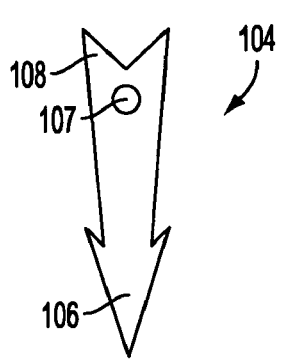
Figure 11D:
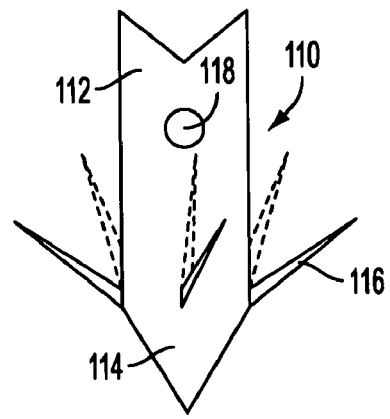

FIGS. 11C and 11D describe alternative embodiments to anchors 90 and 98, respectively. Anchor 104 of FIG. 11C includes barbed distal end 106 similar to that of anchor 90, fixture point 107, and indented proximal end 108 that facilitates delivery of multiple anchors. Specifically, multiple anchors 104 may be loaded into a delivery catheter such that distal end 106 abuts the indentation of proximal end 108 of an adjacent anchor 104, as will be described in greater detail hereinbelow with respect to FIGS. 12A and 12B. Likewise, anchor 110 of FIG. 11D also incorporates indented proximal end 112 in addition to sharp distal end 114, pivoting struts 116 that are expandable from a reduced delivery profile to an expanded profile, and fixture point 118.

Figure 12A:
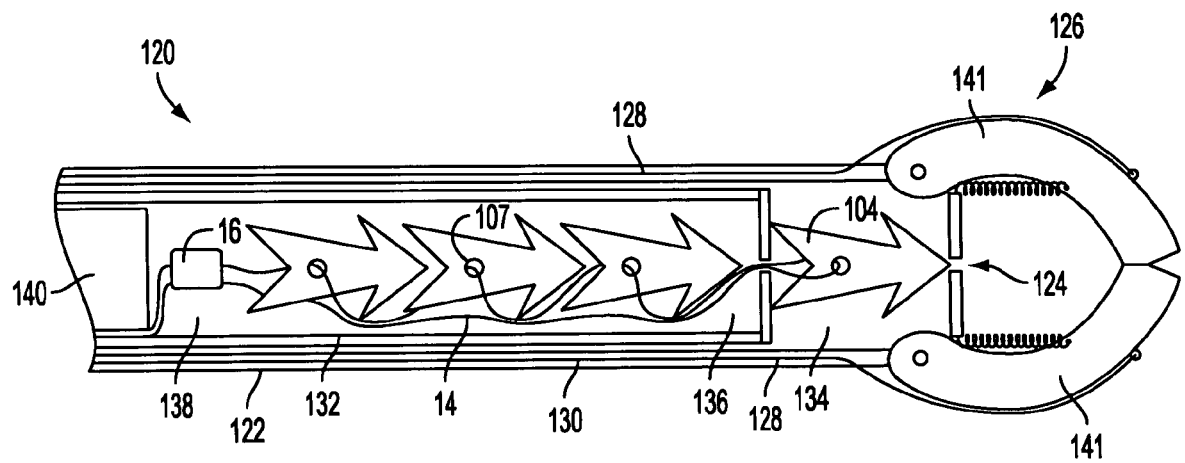
FIGS. 12A and 12B are, respectively, schematic cross-sectional and side views of a delivery catheter for delivering the plurality of anchors of FIGS. 10 and 11A–11D.
Figure 12B:
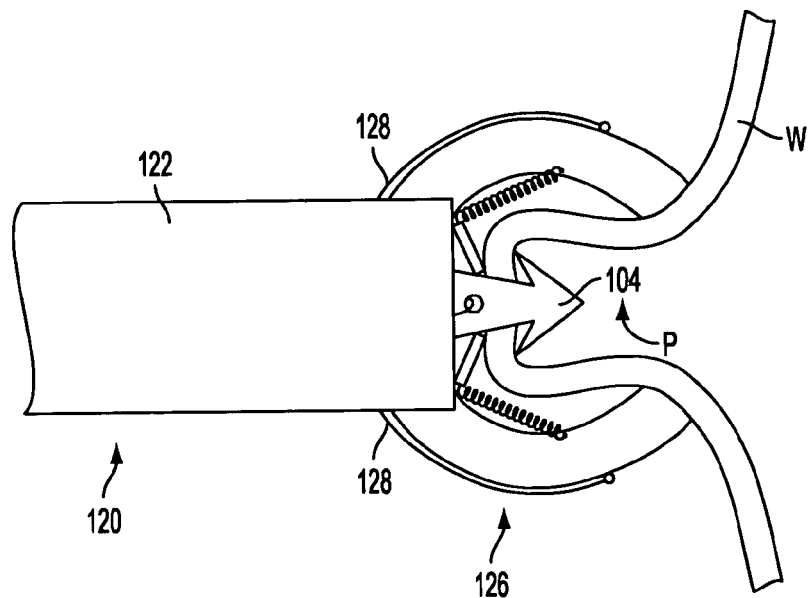

Referring now to FIGS. 12A and 12B, a delivery catheter for delivering the anchors of FIGS. 10 and 11A–11D is described. Delivery catheter 120 includes outer catheter 122 having outer distal end 124, and end effector 126 that is rotatably coupled to outer distal end 124 and that is similar to end effector 66 of FIG. 9. Wires 128 that permit a clinician to control end effector 126 from an actuator (not shown) disposed on a proximal end of delivery catheter 120 are disposed through annular lumen 130 of outer catheter 122. Additional wires (not shown) that enhance steerability of catheter 122 also may be included.

Delivery catheter 120 further comprises inner catheter 132 slidably disposed within central lumen 134 of outer catheter 122. Inner catheter 132 has inner distal end 136 and inner lumen 138, within which plurality of anchors 104 are disposed for delivery to lumen wall W. As discussed hereinabove, drawstring 14 preferably is pre-threaded through fixture points 107 of anchors 104, and fastener 16 preferably is engaged to drawstring 14 prior to disposal of anchors 104 within inner lumen 138 to facilitate delivery of anchors 104. Also disposed within inner lumen 138 proximal to anchors 104 and fastener 16 is push rod 140.

In operation, delivery catheter 120 is advanced through one of the lumens of guide catheter 46 to stomach S. Under the visual guidance of endoscope 50, delivery catheter 120 is maneuvered to dispose end effector 126 adjacent lumen wall W. Wires 128 then are actuated to open pinchers 141 of end effector 126 to grasp the lumen wall therebetween, forming a fold of lumen wall W that defines pocket P distal thereto and that closely approximates outer distal end 124 of outer catheter 122. Thereafter, push rod 140 is distally advanced to urge one anchor 104 through inner distal end 136 into central lumen 134 of outer catheter 122. To determine when one anchor has been ejected from inner catheter 132, indicia (not shown) on a proximal end of delivery catheter 120 may be provided. After one anchor 104 is disposed within central lumen 134 between inner and outer distal ends 136 and 124, inner catheter 132 is advanced distally to urge anchor 104 through outer distal end 124 and into lumen wall W. Further distal advancement of inner catheter 132 relative to outer catheter 122 causes anchor 104 to penetrate through lumen wall W and into pocket P as shown in FIG. 12B. Advantageously, pocket P shields organs, vessel, and/or nerves in the vicinity of the stomach from advancement of anchor 104, thereby decreasing the risk that the anchor may inadvertently damage surrounding tissue during delivery of the anchor.

Figure 13:
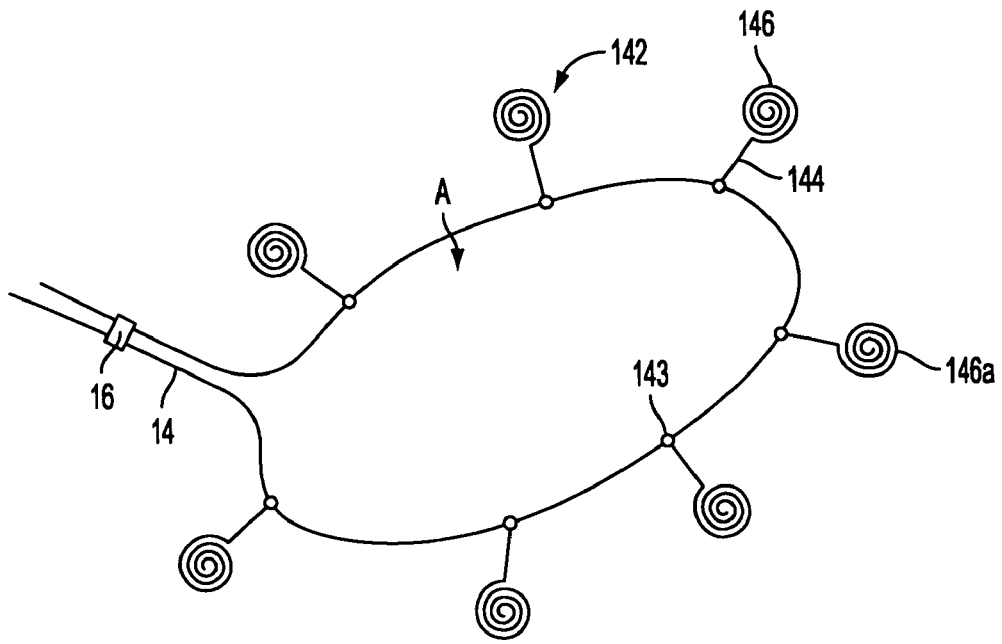
FIG. 13 is a schematic perspective view of yet another alternative embodiment of the plurality of anchors of the present invention.
Figure 15:
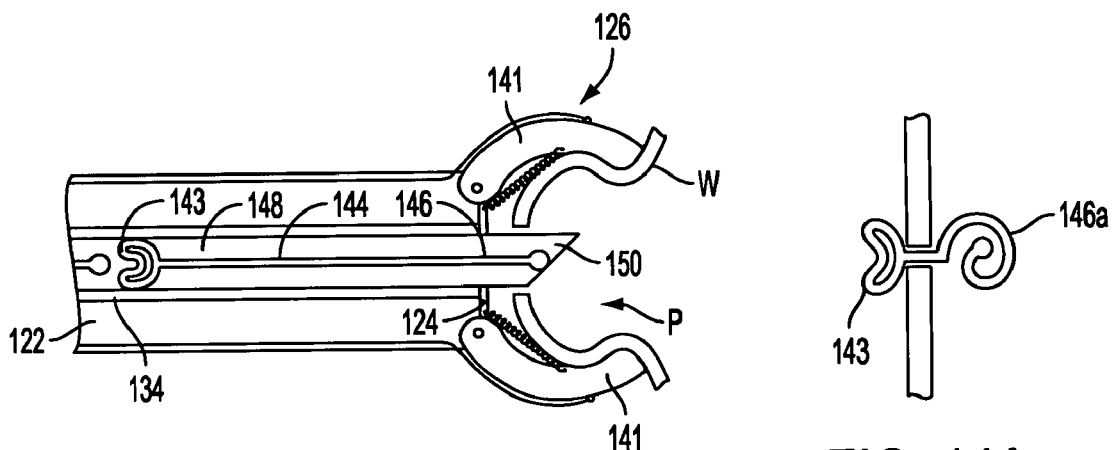
FIG. 15 is a schematic cross-sectional view of a delivery catheter for delivering the plurality of anchors of FIGS. 14A–14C.
Figure 14A:
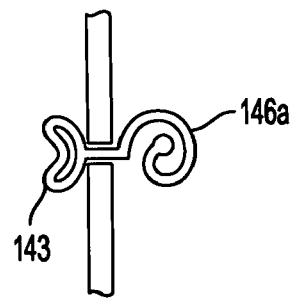
FIGS. 14A–14C are schematic side views of multiple embodiments of the plurality of anchors of FIG. 13.
Figure 14B:
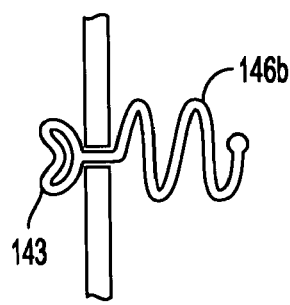
Figure 14C:
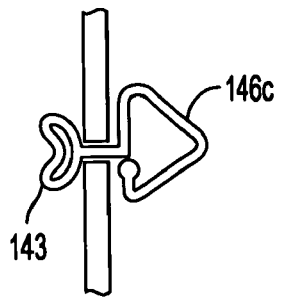

Referring now to FIG. 13, a further alternative embodiment of the plurality of anchors is described. Each anchor 142 comprises fixture point 143 through which drawstring 14 may be threaded, and elongated shaft 144 that may be reconfigured from a reduced delivery profile, as shown in FIG. 15, to an expanded profile. When anchor 142 is disposed in its expanded profile, shaft 144 assumes a coiled shape at distal portion 146 that may be of a spiral configuration (146a in FIGS. 13 and 14A), a zigzag configuration (146b in FIG. 14B), a triangular configuration (146c in FIG. 14C), or combinations thereof. It is contemplated that distal portion 146 also may assume a multitude of other configurations having an expanded profile.

To deliver distal portions 146 of anchors 142 through lumen wall W, anchors 142 are disposed in their reduced delivery profile within catheter 148 (see FIG. 15). Catheter 148 includes sharp distal tip 150 that may penetrate lumen wall W, and a push rod (not shown) that may be distally actuated to urge anchors 142 through distal tip 150. Catheter 148 may be slidably disposed within central lumen 134 of outer catheter 122 of FIGS. 12A and 12B, replacing inner catheter 132. In operation, after pinchers 141 of end effector 126 have grasped a fold of lumen wall W into approximation with distal end 124 of outer catheter 122, catheter 148 is advanced distally through lumen wall W, using sharp distal tip 150 to penetrate therethrough. Thereafter, the push rod distally is advanced through catheter 148 to urge proximal portion 146 of shaft 144 into pocket P. Once proximal portion 146 is advanced past distal tip 150, it assumes its expanded profile. Proximal retraction of catheters 148 and 122 releases the remaining portion of elongated shaft 144 and fixture port 143 therefrom. Contact between expanded proximal portion 146 and a distal surface of lumen wall W prevents anchor 142 from being retracted through lumen wall W back into stomach S.

Figure 16:
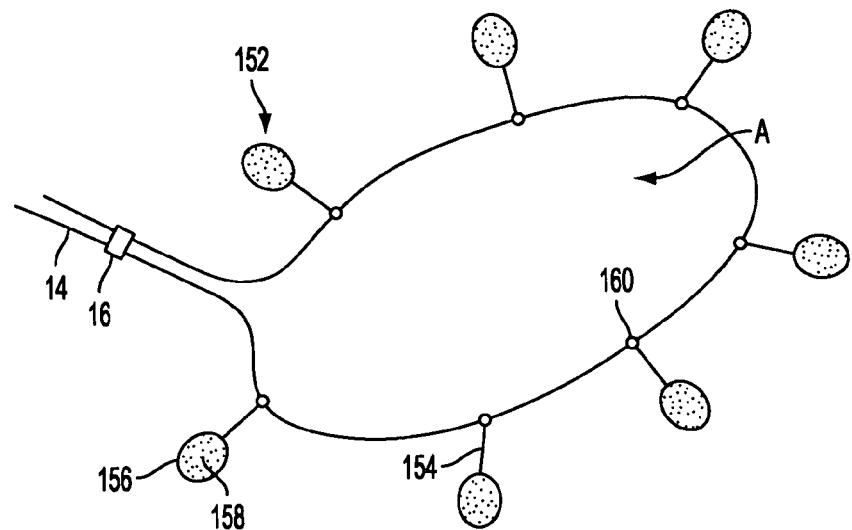
FIG. 16 is a schematic perspective view of still another alternative embodiment of the plurality of anchors of the present invention coupled to the partition of FIG. 1.

Referring now to FIG. 16, yet another alternative embodiment of the plurality of anchors of the present invention is described. Each anchor 152 includes shank 154 coupled to fixture point 160 disposed at the proximal end of shank 154, and to distensible, fluid permeable enclosure 156 that is disposed at the distal end of shank 154 and that contains water-swellable gel 158. Water-swellable gel 158 comprises a substance that may be delivered in a solid granular state, and that swells or increases in volume in the presence of water. One example of a water-swellable gel suitable for use with the apparatus and methods of the present invention is a hydrogel, such as polyacrylamide. A number of synthetic and animal-based hydrogels are known in the art. Catheters 122 and 148 of FIG. 15 may be used to deliver anchors 152.

Figure 17:
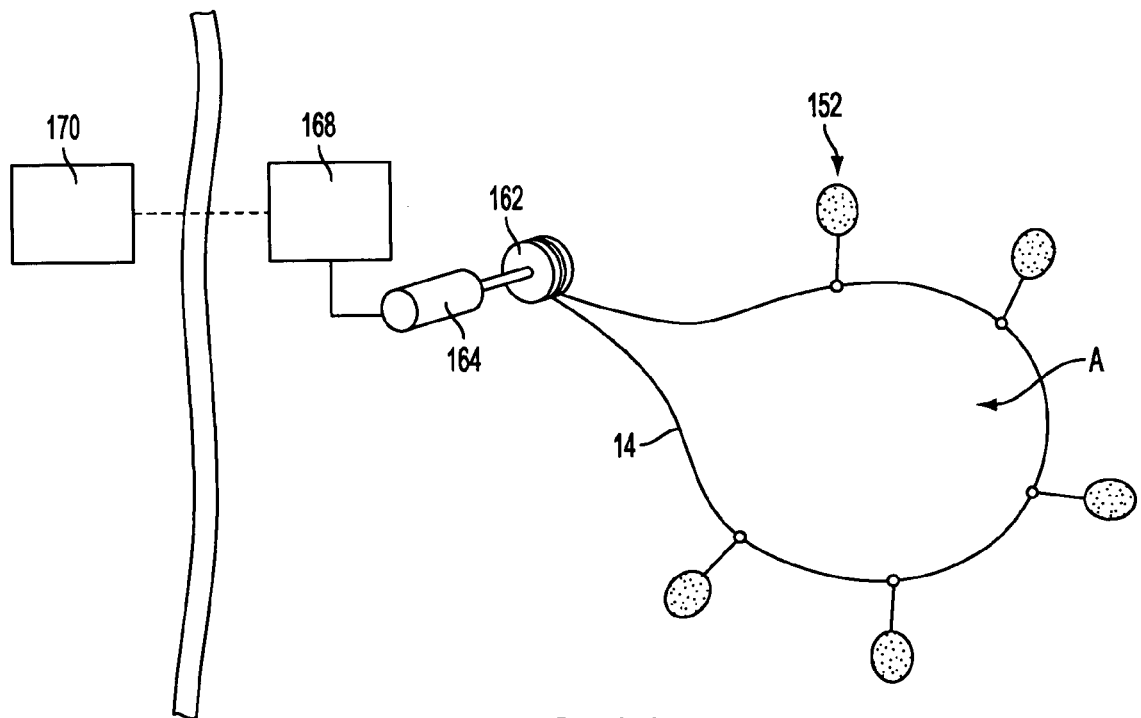
FIG. 17 is a schematic perspective view of the partition of the preceding FIGS. operably coupled to a motor for adjustment of the cross-sectional area defined by the partition.

Rather than endoscopically manipulating fastener 16 to adjust the tension in drawstring 14 and thus adjust the localized reduction in the cross-sectional area of the GI lumen, remote adjustment of drawstring 14 may be provided. As depicted in FIG. 17, drawstring 14 is wound around reel 162, which is coupled to motor 164. Motor 164 is energized by a power source disposed within internal control unit 168, which may be subcutaneously implanted within the patient. Internal control unit 168 further comprises an antenna to receive wireless signals generated and transmitted by external control unit 170, and circuitry that electrically couples and controls motor 164, the power source, and the antenna. External control unit 170 includes a user interface, circuitry to generate a wireless signal for receipt by internal control unit 168, and a signal transmitting antenna to transmit the wireless signal. Suitable motors and control units for use with the apparatus and methods of the present invention are described in U.S. Pat. No. 6,210,347 to Forsell, the entirety of which is incorporated herein by reference. Additional telemetric apparatus and methods also are well known in the art.

In use, a clinician inputs commands into external control unit 170, which generates a wireless signal responsive thereto. The wireless signal is transmitted by the transmitting antenna within external control unit 170, and received by the receiving antenna within internal control unit 168, which then energizes motor 164 to turn reel 166. If the command input by the clinician calls for a reduction in cross-sectional area A, motor 164 will actuate reel 166 to wind an appropriate length of drawstring 14 therearound. Conversely, if the command input by the clinician calls for an increase in cross-sectional area A, motor 164 will actuate reel 166 to unwind an appropriate length of drawstring 14 therefrom. In this manner, the localized reduction in the cross-sectional area of stomach S defined by drawstring 14 may be remotely adjusted.

Referring now to FIGS. 18 and 19, an alternative embodiment of partition 13 of the present invention is described. Partition 13 comprises toroidal balloon 172 having at least one anchor 176 to engage balloon 172 to lumen wall W, and membrane 178, made from a non-extensible material, e.g., Dacron. Membrane 178 is disposed to line balloon 172 to constrain proximal, distal and outward radial expansion of balloon 172 so that adjustments to a volume of inflation medium, e.g., air, water or contrast fluid, within the balloon substantially effects only cross-sectional area A of stoma 174.

In contrast to drawstring 14 and the elongated gastric band described in the "Background of the Invention", the partition of the present embodiment creates a localized reduction in the GI lumen without substantially altering the native shape of the lumen. Balloon 172 creates a partition in the GI lumen and defines stoma 174 having a cross-sectional area smaller than the native cross-sectional area of the GI lumen. To control the rate that food passes through stoma 174 and thus the GI lumen, only cross-sectional area A of stoma 174 substantially is adjusted, e.g., through inflation and deflation of the balloon. Advantageously, without the need to substantially alter the native shape of the GI lumen, the risk of causing trauma is reduced.

To inflate balloon 172 and thereby adjust cross-sectional area A, inflation medium may be endoscopically injected through re-sealable port 184, which is disposed on proximal surface 180 of balloon 172. Re-sealable port 184 is covered by a septum preferably made of silicone, so that the septum will not leak even after repeated punctures.

Alternatively, inflation medium, e.g., air, water or contrast fluid, may be introduced through inflation port 186, which is coupled through tube 188 in fluid communication with balloon 172. Tube 188 preferably comprises a fluid impermeable, substantially non-extensible material, i.e., one having very low compliance, so that the tube does not "absorb" volumes of inflation medium that are intended to be infused into or withdrawn from the balloon. Inflation port 186 incorporates body 190 defining chamber 192, re-sealable septum 194 disposed distal to chamber 192, and stop 196 disposed within chamber 192. Septum 194 preferably is made of silicone, so that the septum will not leak even after repeated punctures by needle 198 of source 200 of inflation medium. Stop 196 prevents needle 198 from puncturing body 190 of inflation port 186 during insertion thereof. Inflation port 186 preferably is encapsulated with silicone and includes a plurality of suture holes for anchoring body 190 to subcutaneous fascia F with septum 194 facing outward in vivo. A puncture may be made through lumen wall W in a manner similar to a percutaneous endoscopic gastrotomy to permit delivery of inflation port 186 to subcutaneous fascia F and disposal of tube 188 across the lumen wall.

Source 200 of inflation medium preferably comprises needle 198, body 202 containing inflation medium, and plunger 204 which may be actuated to inject (or withdraw) inflation medium into (or from) inflation port 186 through needle 198. Needle 198 preferably is non-coring, i.e., the needle will not bore a piece out of septum 194 when inserted into inflation port 186. Source 200 also may comprise optional pressure gauge or transducer 206 to measure and display the pressure in inflation port 186.

In the embodiment of FIG. 18, anchor 176 comprises a substrate having a multiplicity of barbs similar to those described with reference to FIGS. 1–4. It will be apparent to one of ordinary skill in the art that anchor 176 also may comprise a plurality of substrates each having a multiplicity of barbs. Furthermore, anchor 176 also may include any of the anchors described above with reference to FIGS. 10, 11A–11D, 13, 15A–15C and 16, or a combination thereof.

Figure 20:
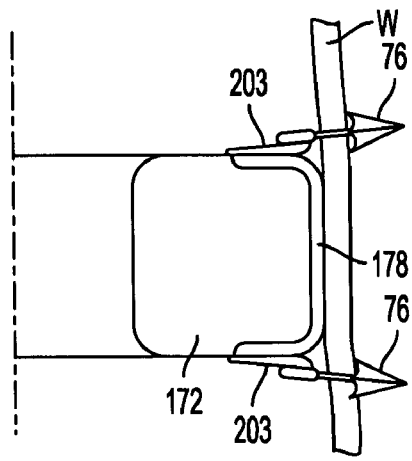
FIG. 20 is a schematic cross-sectional view of two of the plurality of anchors of FIG. 10 coupled to the partition of FIG. 18.

For example, as shown in FIG. 20, balloon 172 may be provided with a plurality of tabs 203 to which anchor 76 of FIG. 10 may be sutured prior to delivery into the GI lumen or after anchors 76 have been embedded within lumen wall W. Tabs 203 may be provided on both proximal and distal surfaces 180 and 182, respectively, so that additional anchors may be coupled to balloon 172 to enhance engagement of balloon 172 with lumen wall W. Furthermore, to counter distally-directed gravitational forces applied by food resting on proximal surface 180 of balloon 172, one or more of anchors 76 may be disposed through lumen wall W in a distally radial direction, as shown in FIG. 20.

Figure 21A:
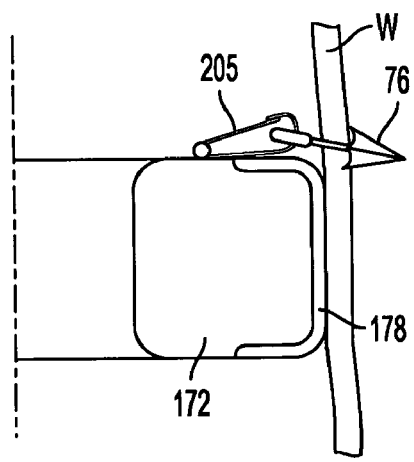
FIGS. 21A and 21B are, respectively, a schematic cross-sectional view of one of the plurality of anchors of FIG. 10 coupled to the partition of FIG. 18 via a latch, and a schematic side view of the latch.
Figure 21B:
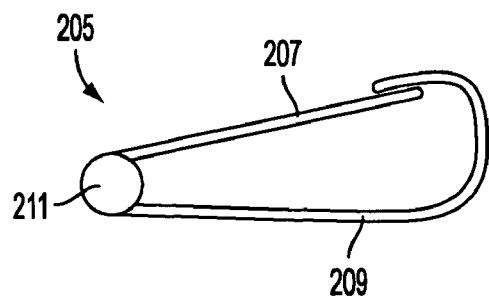

Alternatively, as described in FIG. 21A, one or more tabs 203 may be replaced with a plurality of latches 205 to which anchors 76 may be attached. Detailed in FIG. 21B, latch 205 includes first arm 207, second arm 209 having a J-shape, and torsional spring 211 that biases second arm 209 against first arm 207 to prevent anchor 76 from disengaging from the latch. It will be apparent to one of ordinary skill in the art that additional latch configurations also may be provided.

Figure 22:
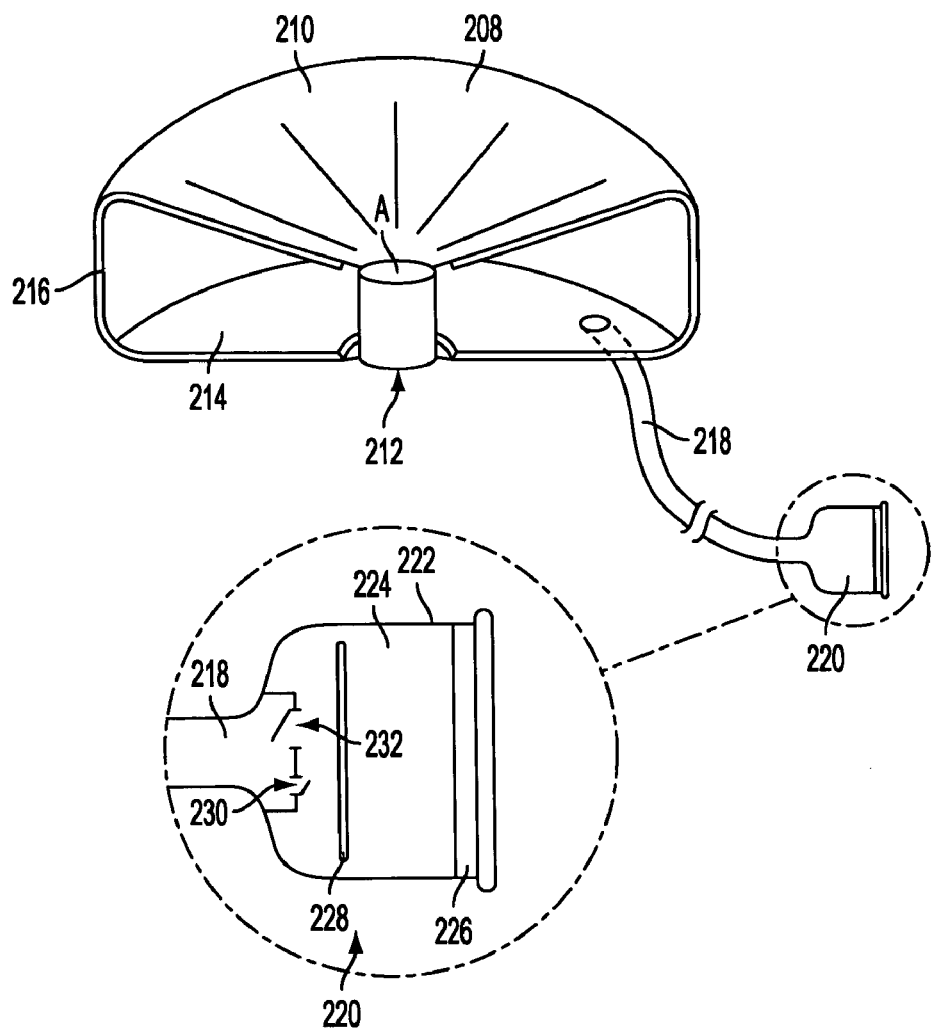
FIG. 22 is a schematic cross-sectional view of an alternative embodiment of the partition of FIG. 18.

In FIG. 22, an alternative embodiment of balloon 172 and inflation port 186 of FIG. 18 is described. Balloon 208 includes proximal surface 210 having an incline that funnels food deposited thereon into adjustable diameter stoma 212, which couples proximal surface 210 and distal surface 214. Balloon 208 also has membrane 216 disposed to constrain proximal, distal and outward radial expansion of balloon 208. Membrane 216 preferably comprises a non-extensible material, e.g., Dacron or polypropylene.

Coupled in fluid communication with balloon 208 via substantially non-extensible tube 218 is inflation port 220. In addition to having compliant body 222 defining chamber 224, septum 226 preferably made of silicone, and stop 228 to prevent a needle of a source of inflation medium from penetrating body 222, inflation port 220 further incorporates unidirectional inflow valve 230 and unidirectional outflow valve 232, both of which preferably are disposed within chamber 224. Inflow valve 230 permits inflation medium to flow from tube 218 into chamber 224 at a rate slower than the rate that outflow valve 232 permits inflation medium to flow in the reverse direction. Illustratively, this effect may be achieved by restricting the opening of inflow valve 230, as compared with the opening of outflow valve 232.

This permits the present invention to dynamically adjust the diameter of stoma 212 responsive to the pressure of food in the GI lumen proximal to proximal surface 210 of balloon 208 in the following manner: In operation, stoma 212 preferably is completely closed or has a small cross-sectional area A in its equilibrium state, i.e., the state in which food is absent. When food enters the GI lumen proximal to balloon 208 and contacts proximal surface 210, the pressure within the balloon exceeds the pressure within chamber 224. The resultant pressure gradient drives inflation medium from balloon 208 to inflation port 220 through restricted inflow valve 230, thereby increasing cross-sectional area A of stoma 212 by partially deflating balloon 208. Inclined proximal surface 210 and increase in the cross-sectional area of stoma 212 facilitates disposal of accumulated food through stoma 212 into a distal portion of the GI lumen. Preferably, to enhance the feeling of satiety and thereby decrease the amount of food consumed, the rate that cross-sectional area A increases is slower than the rate of food consumption.

After all the accumulated food has emptied into the distal portion of the GI lumen, the resulting removal of pressure from proximal surface 210 of balloon 208 causes a shift in the pressure gradient, in which the pressure in inflation port 220 becomes greater than that in balloon 208. This pressure gradient drives inflation medium from inflation port 220 back into balloon 208 to re-inflate the balloon, causing stoma 212 to resume its equilibrium cross-sectional area. Since outflow valve 232 has a bigger opening than that of inflow valve 230, flow of inflation medium back into balloon 208 occurs at a faster rate than flow of inflation medium into inflation port 220. Advantageously, dynamic adjustment of cross-sectional area A of stoma 212 that can be substantially closed prevents a patient from imbibing a liquid diet to compensate for the decrease in solid foods that he may comfortably consume.

Figure 23:
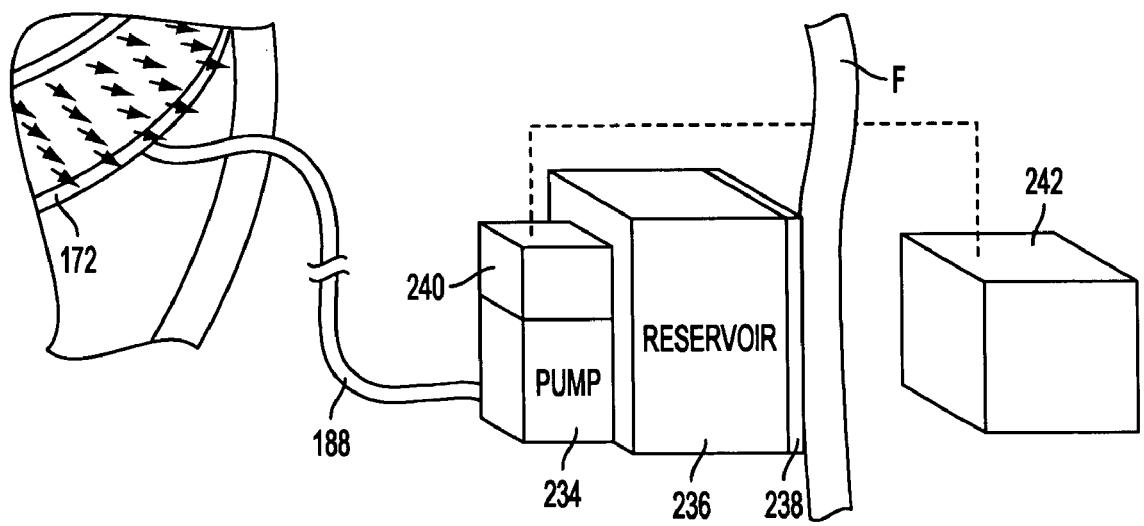
FIG. 23 is a schematic perspective view of a pump and a reservoir for inflation of the partition of FIG. 18.

Pursuant to another aspect of the present invention, stoma 174 defined by balloon 172 may be remotely adjusted. As described in FIG. 23, balloon 172 may be coupled in fluid communication via tube 188 to pump 234 and reservoir 236, both of which preferably are anchored to subcutaneous fascia F. Reservoir 236 also may include septum 238 made of silicone so that additional inflation medium may be introduced as needed through fascia F. Electrically coupled to pump 234 is internal control unit 240.

Similar to internal control unit 168 of FIG. 17, internal control unit 240 also includes a power source to energize pump 234, an antenna to receive wireless signals generated and transmitted by external control unit 242, and circuitry that electrically couples and controls pump 234, the power source, and the antenna. External control unit 242 includes a user interface, circuitry to generate a wireless signal for receipt by internal control unit 240, and a signal transmitting antenna to transmit the wireless signal. Commands input into external control unit 242 are transmitted as wireless signals to internal control unit 240, which then actuates pump 234 to drive inflation medium into or out of balloon 172, depending on whether the cross-sectional area of stoma 174 needs to be decreased or increased, respectively. Suitable hardware for use with the apparatus and methods of the present invention are described in aforementioned U.S. Pat. No. 6,210,347 to Forsell. Additional telemetric apparatus and methods also are well known in the art.

Alternatively, cross-sectional area A of stoma 174 may be adjusted through direct mechanical reduction of the circumference of stoma 174. One example is described in FIG. 24, in which worm gear 244 is disposed around stoma 174 of balloon 172, and engaged to worm 246. To maintain worm gear 244 in a circular shape, buckle 250 is affixed to first end 252 of worm gear 244, and has a slot through which second end 254 may be translatably disposed. Worm 246 is coupled to motor 256, which rotates worm 246 to advance or retract worm gear 244 through buckle 250, thereby decreasing or increasing, respectively, cross-sectional area A of stoma 174. Similar to the apparatus described in reference to FIG. 17, motor 256 is electrically coupled to subcutaneously implanted internal control unit 258, which communicates with external control unit 260 through wireless signals, as described hereinabove.

Referring now to FIG. 25, cross-sectional area A of stoma 174 also may be mechanically adjusted by actuation of thermally-responsive band 262 disposed around stoma 174. Made of a shape memory alloy, e.g., nickel titanium, or an electroactive polymer, band 262 is preformed to transition between an annular configuration having a first diameter and an annular configuration having a second, smaller diameter. To enable the change in diameter, band 262 includes gap 264 located between ends 266 of band 262. Each end 266 is electrically connected via insulated wires 268 to a power source in internal control unit 270, which communicates with external control unit 272 via wireless signals as described hereinabove. When band 262 is energized, it undergoes a phase transition that causes the band to contract from the first diameter into the second, smaller diameter, thereby decreasing the cross-sectional area of stoma 174. To energize and thereby contract band 262, an electrical current may be run through wires 268.

To return band 262 to its non-contracted state, and thereby enlarge cross-sectional area A of stoma 174, a counteracting energizable band (not shown) that is structurally coupled to band 262 may be provided. More specifically, the counteracting band, which is also made of a shape memory material and electrically coupled to internal control unit 270, may be configured to expand from the second diameter to the first diameter when the counteracting band is energized. When the counteracting band expands into the larger diameter, band 262 expands therewith.

Rather than directly energizing band 262, an inductor may be used to heat the band and thereby cause it to contract in diameter. FIGS. 26A and 26B describe band 262 enclosed by at least one toroidal inductor 274. When toroidal inductor 274 is energized, band 262 is inductively heated, causing band 262 to contract in diameter. Exposure to cold water will cause band 262 to return to its non-contracted diameter. Of course, it will be apparent that additional toroidal inductors 274 or other inductor configurations also may be provided.

As previously discussed, illustrative hardware suitable for use with the apparatus and methods of the present invention to remotely adjust cross-sectional area A of stoma 174 are described in U.S. Pat. No. 6,210,347 to Forsell. Additional telemetric apparatus and methods also are well known in the art.

It will be apparent to one of ordinary skill that the remote adjustment mechanisms described hereinabove also may be applied to adjustment of stoma 212 of FIG. 22. Furthermore, the remote adjustment mechanisms described with respect to FIGS. 24–26 also may be used directly with the various types of anchors described in FIGS. 1–4, 10, 11A–11D and 13–15C. For example, drawstring 14 may be replaced by either worm gear 244 or band 262. Worm gear 244 or band 262 may be threaded through fixture points 15 of any of those anchors, and actuated in the manner described above to reduce the cross-sectional area of the stoma defined thereby.

Figure 27:
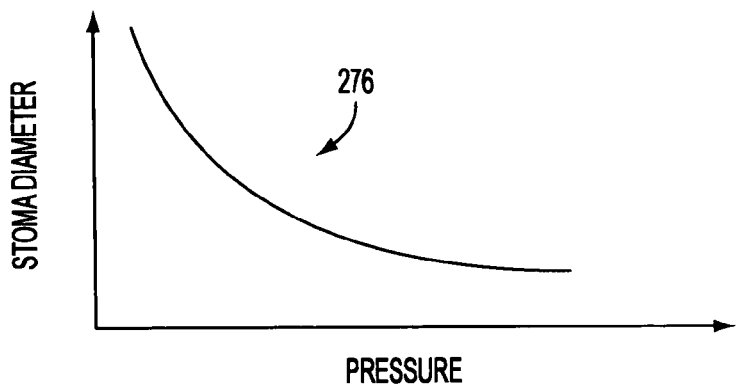
FIG. 27 is a graph of an illustrative relationship between the pressure within the partition of FIG. 18 and a diameter of a stoma defined by the partition.

The diameter of stoma 174 of balloon 172, respectively, may be determined through numerous techniques. One technique relies on provision of a correlation between the diameter of the stoma and the pressure within either the balloon or the inflation port, if present. An exemplary relationship is shown in graph 276 of FIG. 27, in which the stoma diameter is inversely proportional to the pressure within, e.g., inflation port 186. Pressure within inflation port 186 may be measured by pressure gauge or transducer 206 of FIG. 18. Alternatively, a pressure transducer may be disposed within the balloon, and pressure data obtained thereby may be transmitted from an internal control unit similar to those of FIGS. 23, 24 and 25 to an external control unit for display and/or processing. Graph 276 is provided for illustrative purposes only, and in no way should limit the scope of the invention.

Figure 28:
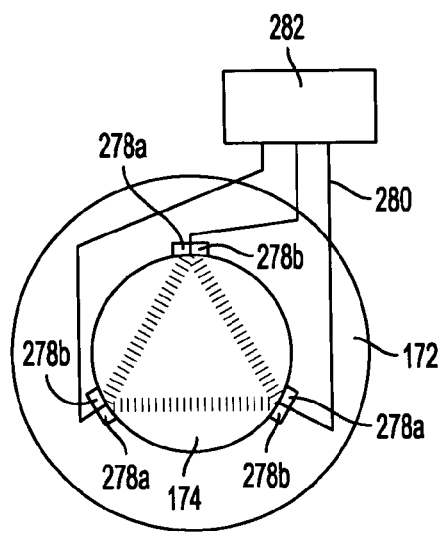
FIG. 28 is a schematic top view of a plurality of ultrasound transducers disposed around a stoma defined by the partition of FIG. 18, the plurality of ultrasound transducers configured to facilitate measurement of a stoma diameter.

Alternatively, as described in FIG. 28, balloon 172 may be provided with plurality of ultrasound transducers 278 disposed around the circumference of stoma 174 at known and preferably equidistant intervals. Each ultrasound transducer 278 includes first crystal 278a to transmit an ultrasound signal to a second crystal 278b of an adjacent ultrasound transducer that receives the signal. Each crystal is electrically coupled via insulated wires 180 to internal control unit 282, which is coupled through wireless transmission to an external control unit (not shown) that processes data provided by the ultrasound crystals. Internal control unit 282 and the external control unit are similar to the control units described with respect to FIGS. 17 and 23–25, and may be integrated therewith.

In operation, after internal control unit 282 receives a command wirelessly transmitted by the external control unit, the internal control unit instructs first crystals 278a to generate and transmit ultrasound signals to second crystals 278b of adjacent ultrasound transducers. Upon receipt of the signals by the second crystals, the time-of-flight of each transmitted signal is determined, and the linear distances between adjacent transducers are calculated. Geometric triangulation of the calculated distances is used to compute the diameter of the stoma.

Figure 29:
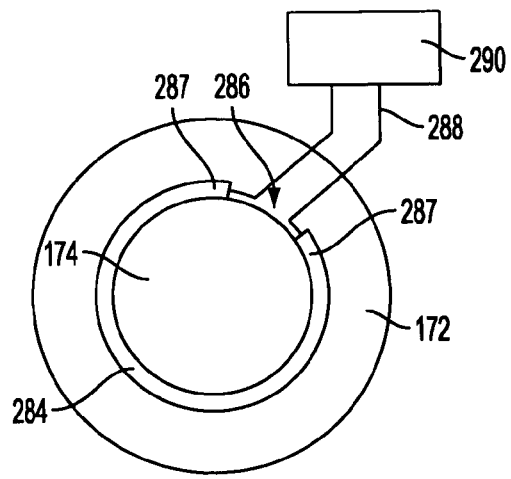
FIG. 29 is a schematic top view of a conductive band disposed around a stoma defined by the partition of FIG. 18, the conductive band having a length-dependent resistance to facilitate measurement of a stoma diameter.

Described in FIG. 29, a further alternative embodiment provides balloon 172 with conductive band 284 disposed around stoma 174. Band 284 has a length that adjusts with the diameter of stoma 174 during inflation and deflation of balloon 172, and gap 286 which accommodates adjustment of the length. Band 284 is made of an elastomeric material encapsulating an electrical element, e.g., one or more variable-length resistors, having an aggregate resistance that is proportional to the length thereof. The electrical element incorporated within band 284 is coupled via insulated wires 288 to subcutaneously implanted internal control unit 290, which preferably has an ohmmeter to facilitate measurement of the resistance of band 284. Internal control unit 290 is adapted to transmit wireless signals to an external control unit (not shown). Internal control unit 290 and the external control unit are similar to the control units described with respect to FIGS. 17 and 23–25, and may be integrated therewith. It will be apparent to one of ordinary skill in the art that band 284 also may be made of other materials having similar properties, such as a conductive polymer having length-dependent resistance.

Figure 30A:
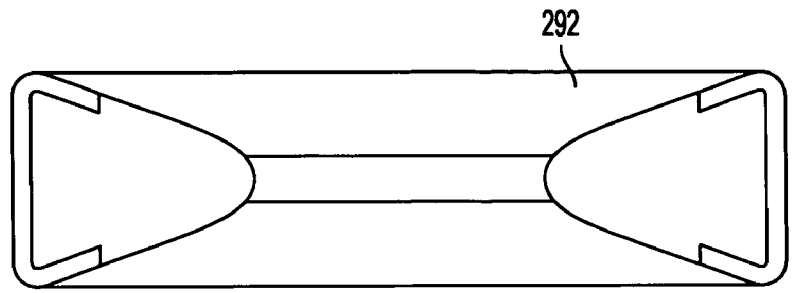
FIGS. 30A and 30B are schematic cross-sectional views of alternative cross-sectional shapes of the partition of FIG. 18.
Figure 30B:
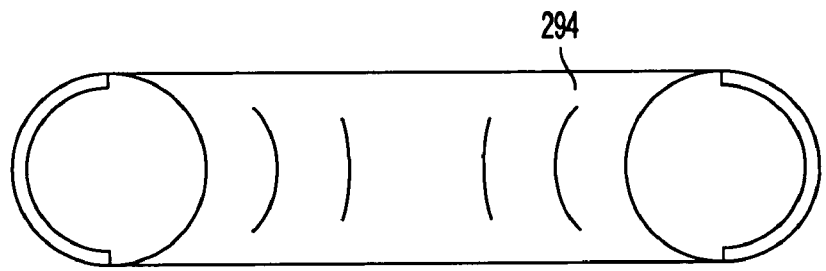

Referring now to FIGS. 30A and 30B, alternative cross-sectional shapes of balloon 172 are provided. FIG. 30A illustrates toroidal balloon 292 having a triangular cross-sectional shape, whereas FIG. 30B describes toroidal balloon 294 having a circular cross-sectional shape. It will be obvious to one of ordinary skill in the art that a variety of other cross-sectional shapes also may be provided without departing from the scope of the invention.

Figure 31:
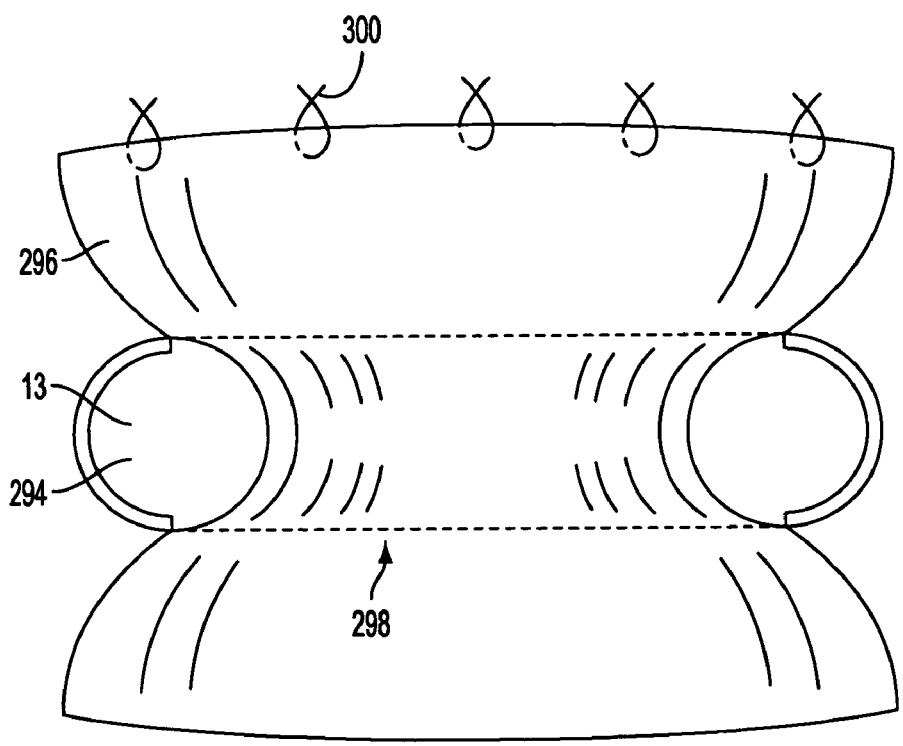
FIG. 31 is a schematic cross-sectional side view of a cuff configured for disposal proximal to the partition of FIG. 30B, and to direct food through a stoma defined thereby.

Pursuant to another aspect of the present invention, partition 13 is designed to create a seal with lumen wall W of the GI lumen to prevent food from shunting past the stoma defined by the partition. For example, as shown in FIGS. 18, 24, 25 and 26A, balloon 172 is designed to have an inflated configuration that sealingly engages lumen wall W. To further decrease the risk of food shunting past the stoma defined by the partition, the present invention also may comprise cuff 296 (see FIG. 31) configured for attachment to lumen wall W proximal to partition 13, e.g., toroidal balloon 294, and disposed through stoma 298 to direct food in the GI lumen to pass through the stoma. The length of cuff 296 preferably may be 1 cm to 15 cm long. Cuff 296 may be made from a flexible biocompatible polymer, and engaged to lumen wall W by sutures 300. Exemplary sutures include sutures having shape memory, e.g., made from a super-elastic material such as nickel titanium, or suture wire typically used in surgical procedures. While FIG. 31 shows cuff 296 configured to direct food over balloon 294, cuff 296 also may be adapted to direct food over any of the partitions herein described.

Figure 32A:
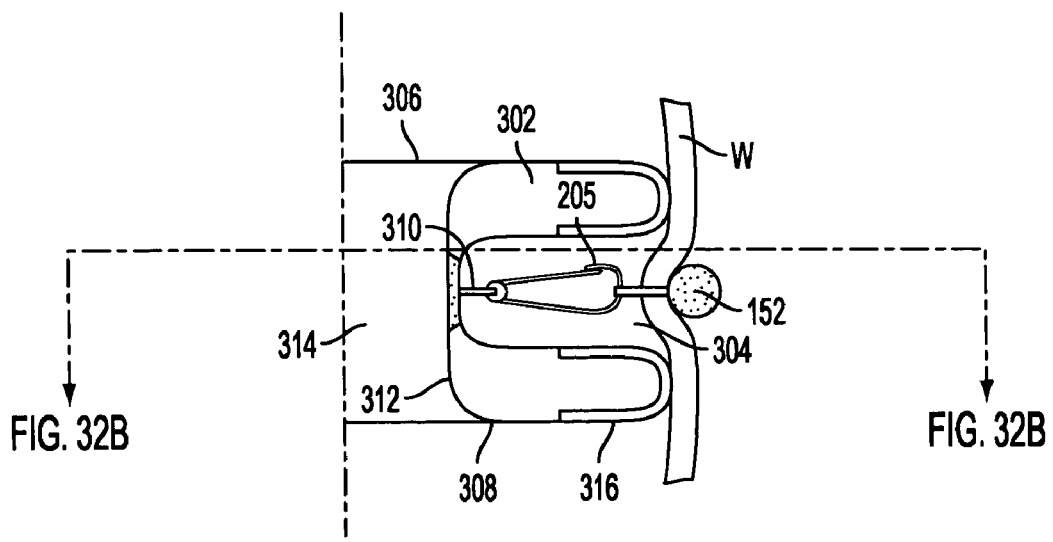
FIGS. 32A and 32B are cross-sectional views of still another alternative embodiment of the partition of FIG. 18 that enhances sealing engagement between the partition and a wall of a GI lumen.
Figure 32B:
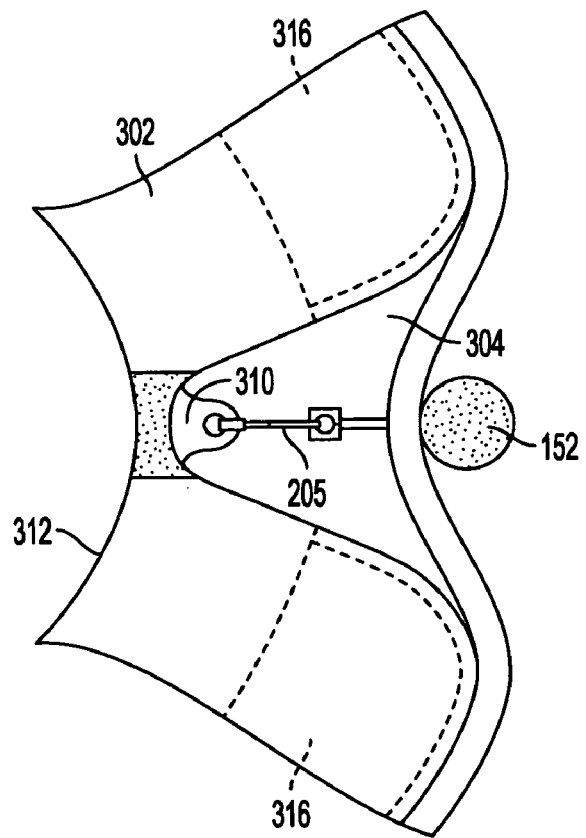

FIGS. 32A and 32B describe yet another alternative embodiment of balloon 172 that further enhances the seal between balloon 172 and lumen wall W. Balloon 302 is similar to balloon 172 except that it also includes plurality of concavities 304 disposed azimuthally around the circumference of the balloon, and preferably mid-depth between proximal surface 306 and distal surface 308. Disposed within each concavity 304 is connector 310 that couples, e.g., anchor 152 of FIG. 16 to balloon 302, either by suturing or use of latch 205 of FIGS. 21A and 21B. Balloon 302 also has inner lateral wall 312, which defines stoma 314, and membrane 316 that constrains expansion of balloon in the proximal, distal and outer radial directions, thereby directing expansion of balloon 302 substantially in the inner radial direction. Connector 310 is coupled to inner lateral wall 312 of balloon 302 so that anchor 152, disposed through lumen wall B, pulls the lumen wall into conformance with concavity 304 when balloon 302 is inflated and the cross-sectional area of stoma 314 consequently is reduced. Connector 310 may be coupled to inner lumen wall 312 by suture, adhesion, or exposure to heat treatment.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. Apparatus for partitioning a gastro-intestinal lumen defined by a lumen wall, comprising:
   a plurality of anchors configured to intraluminally penetrate into the lumen wall, each one of the plurality of anchors providing at least one discrete fixture point movable independently of adjacent fixture points; and
   a partition coupled to the fixture point of each one of the plurality of anchors, the partition providing a localized reduction in a cross-sectional area of the GI lumen, and wherein the partition comprises a biocompatible drawstring defining a stoma.

2. The apparatus of claim 1, wherein at least one of the plurality of anchors comprises a substrate having a multiplicity of barbs.

3. The apparatus of claim 1, wherein at least one of the plurality of anchors comprises a barbed distal end.

4. The apparatus of claim 1, wherein at least one of the plurality of anchors comprises a re-configurable member expandable from a reduced delivery profile to an expanded profile.

5. The apparatus of claim 4, wherein the re-configurable member comprises a plurality of struts.

6. The apparatus of claim 5, wherein the plurality of struts are covered by a membrane.

7. The apparatus of claim 4, wherein the re-configurable member comprises an elongated shaft that assumes a coiled shape when deployed to the expanded profile.

8. The apparatus of claim 1, wherein at least one of the plurality of anchors comprises an enclosure containing a water-swellable gel.

9. The apparatus of claim 1, wherein a cross-sectional area of the stoma is adjustable.

10. The apparatus of claim 1, further comprising:
    an internal control unit configured for subcutaneous implantation and operably coupled to the partition;
    an external control unit that emits wireless signals for receipt by the internal control unit.

11. The apparatus of claim 1, further comprising a cuff configured for attachment to the lumen wall proximal to the plurality of anchors and the partition, and to direct food in the GI lumen to pass through a stoma defined by the partition.

12. The apparatus of claim 1, further comprising a plurality of latches configured to couple the partition to the fixture point of each one of the plurality of anchors.

* * * * *